US012539192B2

(12) United States Patent
Schiffman et al.

(10) Patent No.: US 12,539,192 B2
(45) Date of Patent: Feb. 3, 2026

(54) JAW SUPPORT DEVICE

(71) Applicant: The Restful Jaw Company, LLC, Saint Paul, MN (US)

(72) Inventors: Eric Schiffman, Saint Paul, MN (US); Anna Heithoff, Minneapolis, MN (US); Troy Pongratz, Saint Paul, MN (US); Michael David Weston, Minneapolis, MN (US)

(73) Assignee: THE RESTFUL JAW COMPANY, LLC, Saint Paul, MN (US)

( * ) Notice: Subject to any disclaimer, the term of this patent is extended or adjusted under 35 U.S.C. 154(b) by 579 days.

(21) Appl. No.: 17/135,855

(22) Filed: Dec. 28, 2020

(65) Prior Publication Data

US 2021/0113291 A1 Apr. 22, 2021

Related U.S. Application Data

(63) Continuation of application No. PCT/US2019/039930, filed on Jun. 28, 2019.

(Continued)

(51) Int. Cl.
*A61G 13/12* (2006.01)
*A61B 90/14* (2016.01)
(Continued)

(52) U.S. Cl.
CPC .............. *A61B 90/14* (2016.02); *A61G 13/12* (2013.01); *A61G 15/125* (2013.01);
(Continued)

(58) Field of Classification Search
CPC ...... A61F 5/3707; A61F 5/3792; A61F 5/055; A61F 5/05891; A61F 5/05883;
(Continued)

(56) References Cited

U.S. PATENT DOCUMENTS

| | | | |
|---|---|---|---|
| 571,209 | A | 11/1896 | Adams |
| 678,417 | A | 7/1901 | Muller |

(Continued)

FOREIGN PATENT DOCUMENTS

| | | | |
|---|---|---|---|
| GB | 2194156 | A | 3/1988 |
| GB | 2479066 | A | 9/2011 |

(Continued)

OTHER PUBLICATIONS

Patricia Guimaraes Fernandes; A randomized control clinical trial evaluating the usefulness of an external mandibular support device during dental care in TMD patients; Thesis; 2008; pp. 2-4, 22.

(Continued)

*Primary Examiner* — Adam Baker
(74) *Attorney, Agent, or Firm* — GRUMBLES LAW PLLC; Brittany Haanan

(57) ABSTRACT

A jaw support device for supporting a patient's jaw during dental procedures. More specifically, a jaw support device comprising a headrest mount assembly, a split sphere assembly having a first locking mechanism, a ball joint assembly having a second locking mechanism, and a jaw rest assembly. The headrest mount assembly may attach to a dental chair headrest. The split sphere assembly may have a split sphere ball and an arm extension and may attach to the headrest mount assembly. Further, the split sphere assembly's first locking mechanism may lock the arm extension in place. The ball joint assembly may have a ball joint ball and may connect to the arm extension of the split sphere assembly. The jaw rest assembly may attach to the ball joint assembly and may be locked in place when the second locking mechanism is activated.

20 Claims, 14 Drawing Sheets

Related U.S. Application Data

(60) Provisional application No. 62/691,306, filed on Jun. 28, 2018.

(51) Int. Cl.
*A61G 15/12* (2006.01)
*A61B 90/57* (2016.01)

(52) U.S. Cl.
CPC .... *A61B 2090/571* (2016.02); *A61G 2200/34* (2013.01); *A61G 2200/50* (2013.01); *A61G 2203/78* (2013.01)

(58) Field of Classification Search
CPC ........ A61G 15/02; A61G 15/08; A61G 15/10; A61G 15/12; A61G 15/125; A61G 7/1084; A61G 7/072; A61G 7/0506
USPC ............ 602/18, 17, 16, 12, 32, 36; 128/845, 128/846, 847
See application file for complete search history.

(56) References Cited

U.S. PATENT DOCUMENTS 837,612 A 12/1906 Davis
1,356,365 A 10/1920 Hosmer
1,397,499 A 11/1921 Brennan
1,729,525 A 9/1929 Stenshoel
1,885,507 A * 11/1932 Browne ............... A61G 15/125 297/409
2,223,276 A 11/1940 Ward
2,630,342 A * 3/1953 Gilmont ................ F16B 7/0486 403/53
2,652,221 A * 9/1953 Kampa ................... B60R 1/078 248/276.1
2,692,595 A 10/1954 Blair, Jr.
2,735,424 A 2/1956 Benjamin
2,820,455 A 1/1958 Hall
2,904,040 A 9/1959 Hale
3,224,439 A 12/1965 Blair, Jr.
3,317,244 A * 5/1967 Ferro ................... A61G 15/125 297/410
3,724,452 A 4/1973 Nitschke
3,878,840 A 4/1975 Esbelin
4,374,497 A * 2/1983 Harmand ................. B23Q 1/28 108/4
4,628,913 A 12/1986 Lerman
4,793,334 A 12/1988 McGuinness et al.
5,054,475 A 10/1991 Calabrese et al.
5,201,702 A 4/1993 Mars
5,208,928 A 5/1993 Kuck et al.
5,332,287 A 7/1994 Whitmyer
5,409,450 A 4/1995 Donelson
5,433,696 A 7/1995 Osti
5,531,669 A 7/1996 Varnau
5,803,642 A * 9/1998 Sassmannshausen ....................... F16C 11/0604 403/90
5,918,844 A * 7/1999 Ognier ................. F16M 13/022 269/74
6,267,741 B1 7/2001 Lerman
6,368,295 B1 4/2002 Lerman
6,419,321 B1 * 7/2002 Sack ........................ A61G 5/12 297/405
7,029,500 B2 4/2006 Martin
7,117,551 B1 * 10/2006 Dinkler, II ............ A61G 13/12 5/637
7,393,057 B2 7/2008 Fraser
7,500,480 B2 3/2009 Matula, Jr. et al.
7,549,970 B2 6/2009 Tweardy
7,730,563 B1 6/2010 Sklar et al.
7,789,843 B2 9/2010 Ray
D631,969 S 2/2011 King et al.
D634,015 S 3/2011 King et al.
8,001,633 B2 8/2011 Swain, Jr.
8,057,415 B2 11/2011 Hipp et al.
8,529,482 B2 9/2013 Giontella
8,864,694 B2 10/2014 Schiffman et al.
8,911,019 B2 * 12/2014 Josten ...................... G05G 1/01 297/405
9,572,741 B2 * 2/2017 Weaver ................. A61F 5/3723
2001/0039680 A1 11/2001 Boucher et al.
2002/0014567 A1 * 2/2002 King ...................... F16M 11/14 248/276.1
2004/0123389 A1 * 7/2004 Boucher ................ A61G 13/12 5/621
2005/0010148 A1 1/2005 Bonutti
2005/0245854 A1 11/2005 Leuthardt et al.
2006/0217648 A1 9/2006 Rogachevsky
2008/0034502 A1 2/2008 Copeland et al.
2009/0145443 A1 6/2009 Dreyfuss
2009/0187129 A1 7/2009 Ben-Galim et al.
2012/0124748 A1 5/2012 Soto et al.
2013/0247919 A1 * 9/2013 Chauvette .............. A61B 90/14 128/845
2015/0025433 A1 1/2015 Schiffman et al.
2017/0202638 A1 7/2017 Schiffman et al.

FOREIGN PATENT DOCUMENTS

JP S58108820 U 7/1983
JP 2008264007 A 11/2008
JP 2012020101 A 2/2012
RU 110636 U1 11/2011
WO 0149223 A1 7/2001
WO 2013163447 A2 10/2013
WO 2016036997 A1 3/2016

OTHER PUBLICATIONS

SOMI Brace; product catalogue; 1995; http://trulife.com/all-products/orthotics/cervical/cto/somi-brace.
Terry Gene Zucuskie; A Controlled Clinical Trial of the Usefulness of an External Mandibular Support Device During Routine Dental Care; Thesis; Jun. 21, 1996; pp. 4-5.
Hypnoz Therapeutic Devices, Inc.; Our Products; Website; http://www.hypnozdevices.com/?page_id=14.
Non-Final Office Action for U.S. Appl. No. 13/457,376; date of mailing: Dec. 19, 2013; date of filing: Apr. 26, 2012; 13 pp.
International Search Report of International Application No. PCT/US2013/038246; date of mailing: Oct. 2, 2013; date of filing: Apr. 25, 2013; 2 pp.
Japanese Office Action for J.P. Application No. 2015-509145; date of mailing: Jul. 5, 2016; date of filing: Apr. 25, 2013; 4 pp (translation 3 pp).
European Search Report for E.P. Application No. 13781660.9; date of mailing: Nov. 9, 2015; date of filing: Apr. 25, 2013; 7 pp.
Non-Final Office Action for U.S. Appl. No. 14/476,516; date of mailing: Dec. 27, 2017; date of filing: Sep. 3, 2014; 10 pp.
Final Office Action for U.S. Appl. No. 14/476,516; date of mailing: Jul. 17, 2018; date of filing: Sep. 3, 2014; 11 pp.
International Search Report and Written Opinion of International Application No. PCT/US2015/048419; date of mailing: Dec. 4, 2015; date of filing: Sep. 3, 2015; 9 pp.
Non-Final Office Action for U.S. Appl. No. 15/448,059; date of mailing: Jun. 12, 2019; date of filing: Mar. 2, 2017; 10 pp.
International Search Report and Written Opinion of International Application No. PCT/US2019/039930; date of mailing: Sep. 13, 2019; date of filing: Jun. 28, 2019; 7 pp.
Supplemental Examination Report pertaining to European Patent Application No. 19824585.4, dated Feb. 18, 2022.
Office Action pertaining to corresponding Chinese Patent Application No. 201980043903.9, issued Mar. 23, 2022.
Office Action pertaining to corresponding Japanese Patent Application No. 2020-572519, issued Jun. 28, 2023.

* cited by examiner

JAW SUPPORT DEVICE

FIELD OF THE DISCLOSURE

The disclosed invention relates to a medical device used to support a patient's jaw during dental procedures. More specifically, the device can stabilize the patient's jaw in situations where downward forces create risk of injury and are counterproductive to a procedure the patient is undergoing.

BACKGROUND OF THE INVENTION

Individuals with temporomandibular disorders (TMD) suffer from a variety of symptoms including pain in and around the temporomandibular joint (TMJ) and jaw muscles, headaches, restricted mouth opening or closing, TMJ noises, and many other symptoms including ear and neck pain. While there are several hypothesized causes of TMD, dental treatment for people with TMD can be challenging due to the jaw pain they are already experiencing and the extra time dentists need to provide patients with during procedures so patients can be given time to rest their jaws.

Additionally, overextension or significant force on the jaw during dental treatments is a major cause of TMD, and TMD complaints result in uncompensated postoperative care. Currently, approximately 5 to 12% of the population suffers from TMD or TMD-like symptoms. Most of these people are women between the ages of 18 and 45.

Even for those patients who do not suffer from TMD, dental procedures can cause jaw pain, discomfort and fatigue from opening the mouth too long, too wide or by placing too much downward force on the jaw. When downward forces are applied to a patient's jaw during dental procedures, the patient must tense their jaw muscles to counter the downward force, and this action often contributes to jaw pain and injury. Further, if a patient is sedated, the patient may have no way of knowing that downward force is being used and cannot tense their jaw muscles to oppose the downward force, which increases the risk of overextending the jaw and causing injury. Injury to a patient can result in: (1) lost time for the dentist to manage the symptomatic patient; (2) patient suffering and injury; and (3) potential medico-legal problems.

While current medical devices in the dental market exist to prop the mouth open (i.e., bite blocks), these do not support the jaw when downward forces are applied. Additionally, dentists attempt to address patient safety by supporting the patient's jaw with their own or their assistant's hands, limiting procedure time, terminating the procedure if the patient complains of pain, or providing breaks during procedures. However, these current methods are not always effective and can be disruptive to a procedure. Therefore, a new device is needed that supports the jaw when a downward force is applied, prevents over extension of the jaw, minimizes jaw pain and fatigue during dental procedures, and reduces treatment time.

SUMMARY OF THE INVENTION

The disclosed jaw support device can hold a patient's jaw in one position and provide stability for a dentist to do complex dental procedures with minimal jaw movement and fewer patient time breaks. More specifically, the jaw support device includes one or more jaw rests for holding a patient's jaw in a fixed relative position. The jaw support is itself supported in its fixed position using additional mechanisms such as one or more arms that can be attached to a dental, oral surgical, or other health professional chair (e.g., otolaryngological). The jaw support device is used to support the patient's jaw.

In one example, the jaw support device includes a headrest mount assembly structured and configured to attach to a dental chair headrest; a split sphere assembly having a split sphere ball and an arm extension, wherein the split sphere assembly attaches to the headrest mount assembly; a ball joint assembly having a ball joint ball, wherein the ball joint assembly connects to the arm extension; and a jaw rest assembly configured to attach to the ball joint assembly; wherein the split sphere ball is structured and configured to be pressurized to lock the arm extension in place, and the ball joint ball is structured and configured to be pressured to lock the jaw rest assembly in place.

DETAILED DESCRIPTION

Figure 1:
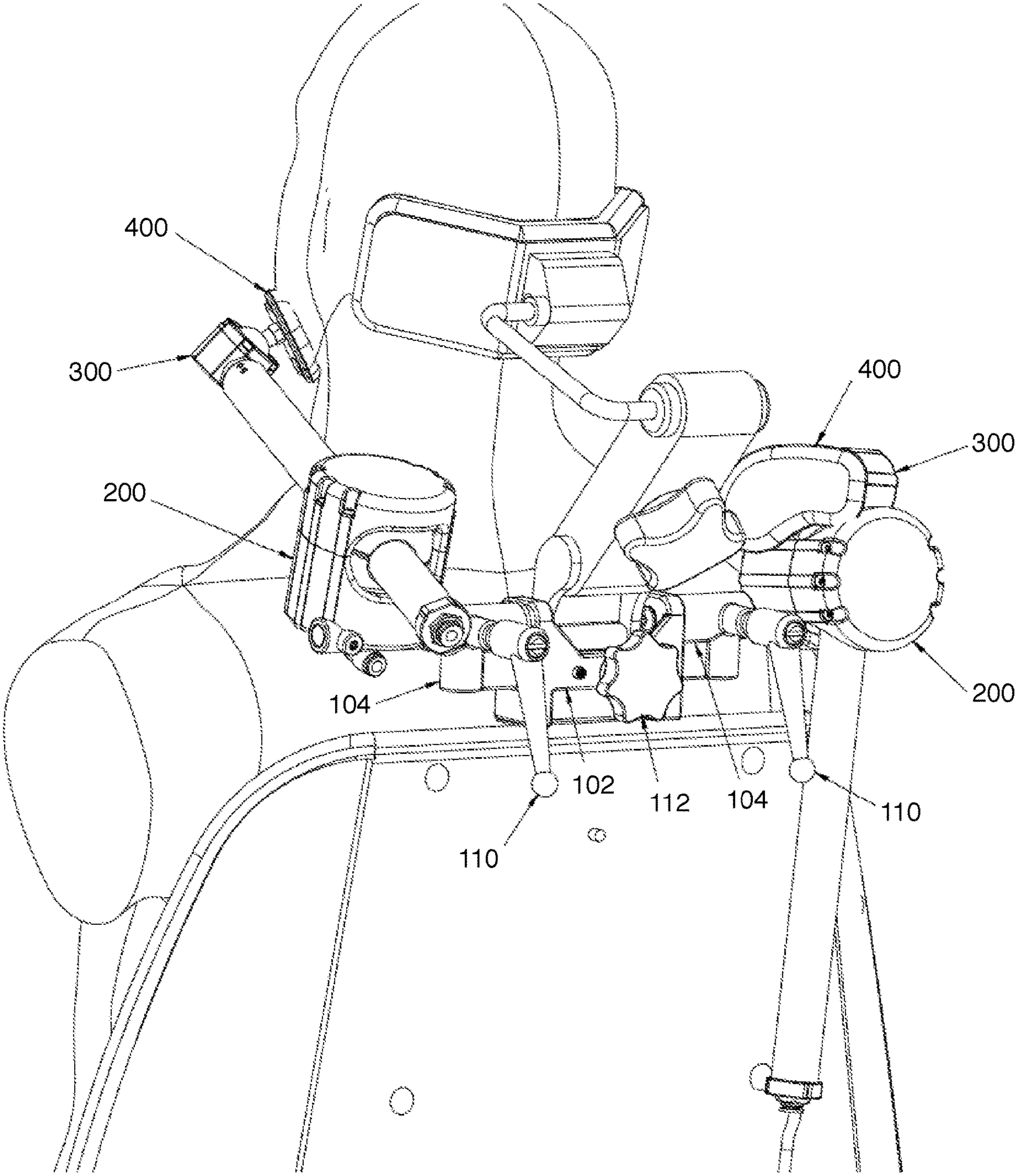
FIG. 1 is a perspective back view of one embodiment of the disclosed jaw support device while in use.

Various user interfaces and embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims. It is understood that various omissions and substitutions of equivalents are contemplated as circumstances may suggest or render expedient, but these are intended to cover application or embodiments without departing from the spirit or scope of the claims attached hereto. Also, it is to be understood that the phraseology and terminology used herein are for the purpose of description and should not be regarded as limiting.

The jaw support device is fitted to a patient's jaw and fitted by a trained user, often times a dental professional, to assist in alleviating patients' jaw pain and to reduce fatigue during and after dental procedures. It can be designed to provide the required jaw support with minimal restriction on jaw movement and minimal intrusion into the dental operating field.

The jaw support device can alleviate pain and fatigue during dental procedures by supporting the jaw and allowing the patient to refrain from actively resisting pressure from the dentist when a downward force is applied. This allows the dentist to place the amount of pressure required on the jaw without worrying about inflicting pain on the jaw, hyper-extending the jaw, taking breaks to allow the patient to rest, or providing care for sore jaw muscles or TMJs.

Several types of patients can benefit from the disclosed device: (1) patients undergoing long procedures—especially on the mandibular arch; (2) patients undergoing any procedure where significant force is placed on the mandibular arch including the mandibular teeth; (3) symptomatic TMJ/TMD patients; (4) asymptomatic patients with signs of TMD; (5) patients who experience over-extension of the jaw or locking open; (6) patients with movement disorders such as Tardive Dyskinesia, Parkinson's, MS; (7) and geriatric patients.

The device, in some embodiments, can be attached to a chair, such as a dental chair, and can be adjusted to comfortably fit a patient's jaw. The support for the jaw, which can be one or more jaw rests, can be attached to an arm that can attach to, for example, a headrest or post of the dental procedure chair. The jaw rest can include a pad made of one or more foam layers (such as compressible foam) or any other reasonably firm, yet viscoelastic material that is resilient and flexible and allows the patient's jaw to rest comfortably on the jaw rest. The jaw rest can be adjustable to ensure that it properly supports the jaw. In some embodiments, it may be located on a ball joint that enables adjustability and rotation in all directions.

The jaw support device can have at least two main parts, an arm and a jaw rest, if the assembly is built into the dental chair. If the jaw support device is not built in to the dental chair, it can have at least three main parts: an arm, a jaw rest, and a headrest attachment piece that can connect the arm to the existing dental chair. The benefit to these embodiments is that the dental chair supports the jaw support device.

The arm can operate in several ways. In one embodiment, the arm can be an articulating arm that includes two or more rods or other rigid support structures connected via pivot hinges. The first rod can connect to the dental chair or the headrest attachment piece. The other end of the first rod can connect to the second rod. The second rod can be connected, on its other end, to either the jaw rest or a third arm. These connections can continue so as to include any number of rods. This construction allows the user to custom fit the jaw support device to a patient. Additionally, the jaw support device, in this embodiment, can fold away behind the chair or on the side of it.

In another embodiment, the arm can be a straight or a curved telescoping arm with rotational joints. For example, the telescoping arm can include a plurality of rods, each capable of sliding into the rod next to it for storage. The first telescoping rod, which is closest to the dental chair, can connect directly to the dental chair or indirectly to the dental chair via a headrest attachment piece. The last telescoping rod, which is furthest from the chair and closest to the patient's jaw, can connect, on one end, directly to the jaw rest and, on the second send, either directly to the first telescoping rod or indirectly to the first telescoping rod via one or more inner telescoping rods. When in use, the user can slide one or more of the rods out from each other and lock them in place at each joint. The rods can also be locked in place when they slide into one another. For example, a second rod can be extended and locked to a first rod, and a third rod can slide in and lock to the second rod. In this way, the length of the arm can vary based on the user's needs. Each lock can also include a rotational joint, enabling the user to custom fit the jaw support device to a patient. The locks at each joint can be, for example, manual locks or electrical or pneumatic locks.

Figure 20:
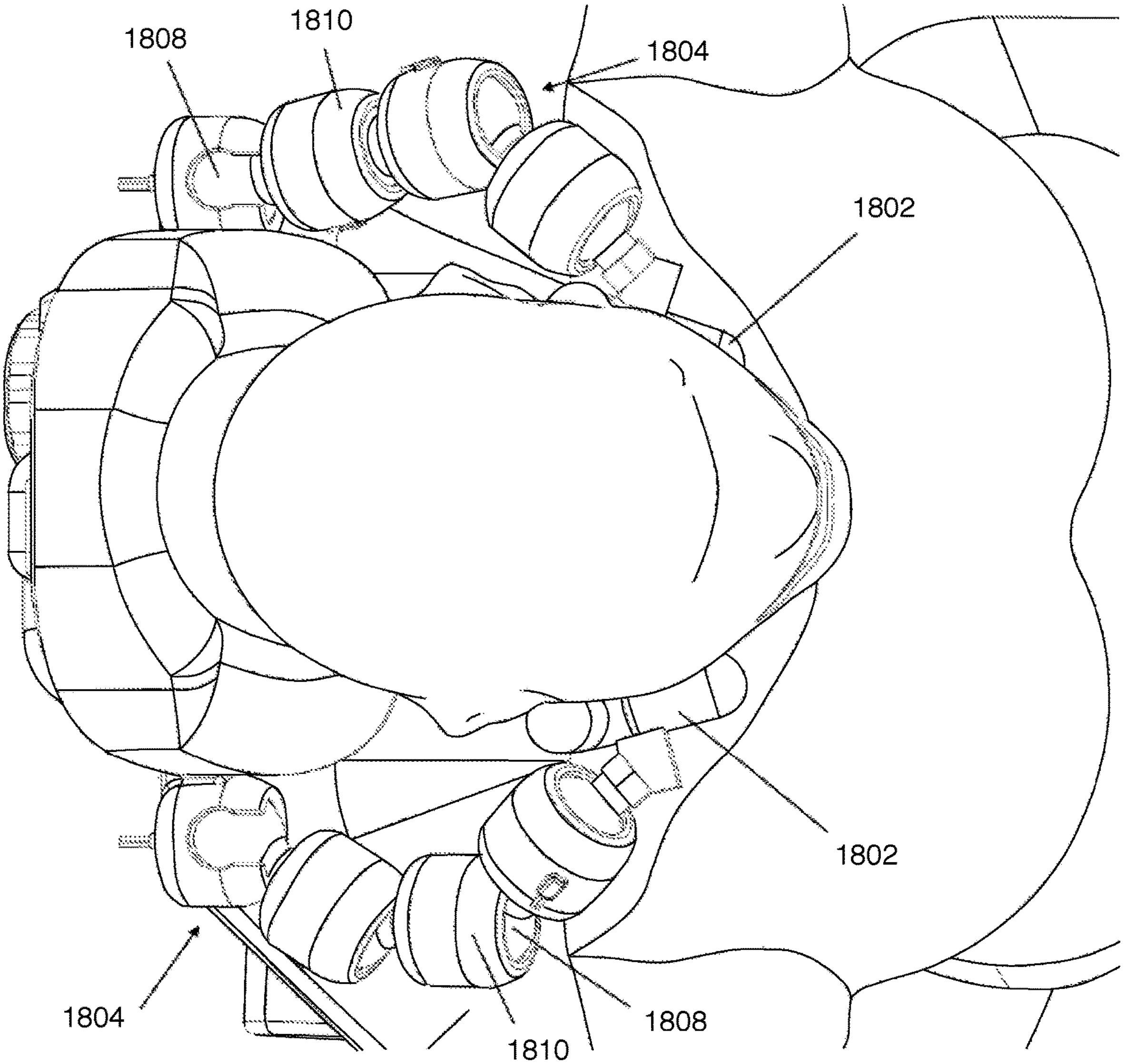
FIG. 20 is a top view of one embodiment of the disclosed jaw support device in use.
Figure 21:
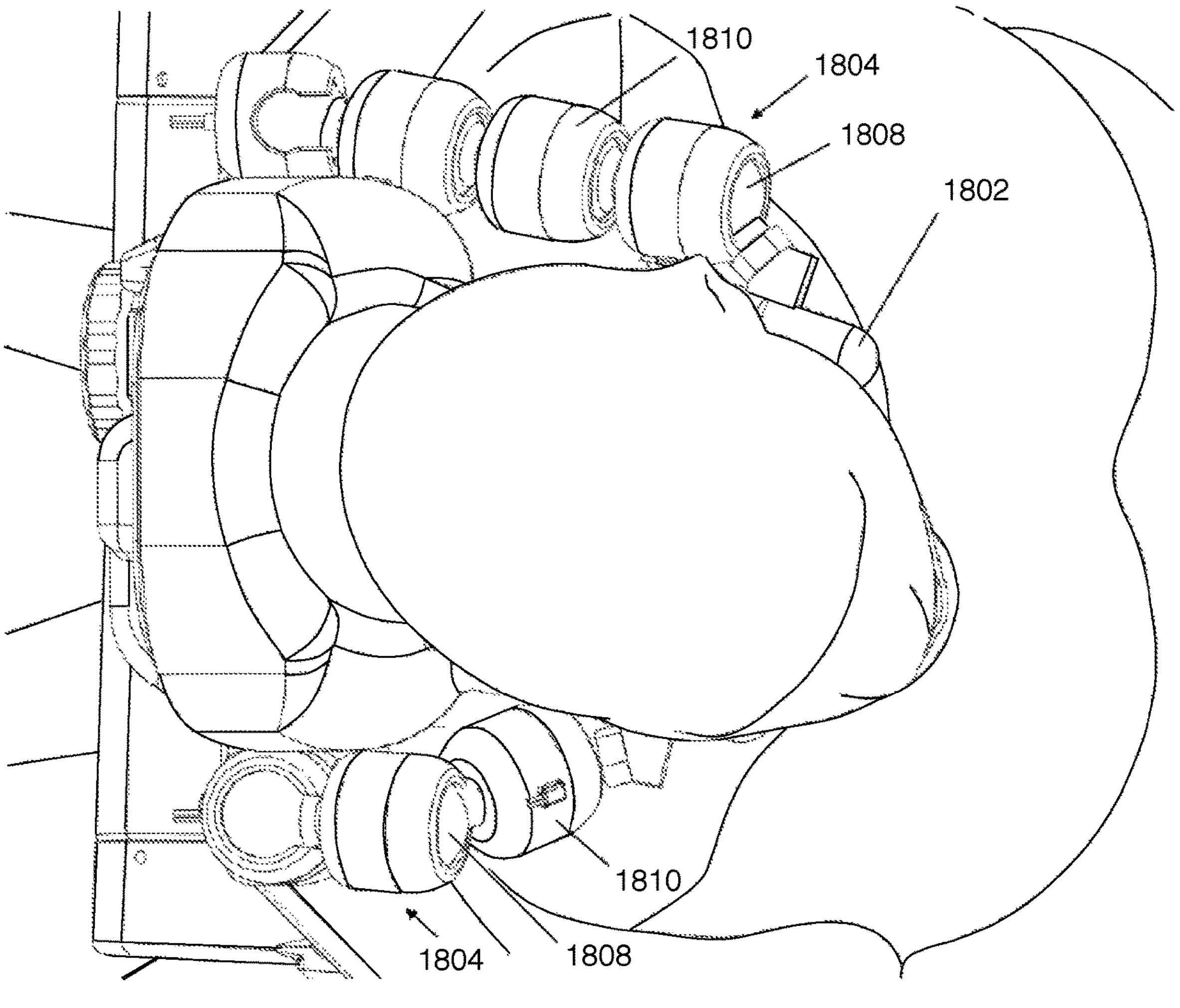
FIG. 21 is a top view of one embodiment of the disclosed jaw support device in use and illustrates the jaw support device holding a patient's jaw at a 30-degree angle.

In some embodiments, as described above, the jaw support device can have two arms, as illustrated in FIG. 1. In this embodiment, one end of each arm can connect directly to the dental chair or indirectly to the dental chair via a headrest attachment piece. Therefore, a first arm can protrude from the left side of the dental chair and a second arm can protrude from the right side of the dental chair. The first and second arms can then wrap around their respective sides of the patient in the dental chair. In some embodiments, the arms can connect, in front of the patient, to each other using an arm-to-arm locking mechanism. This embodiment can reduce stress on the joints of the first and second arms. In other embodiments, as illustrated in FIGS. 1 and 20-21, the arms to do not lock to each other.

Figure 2:
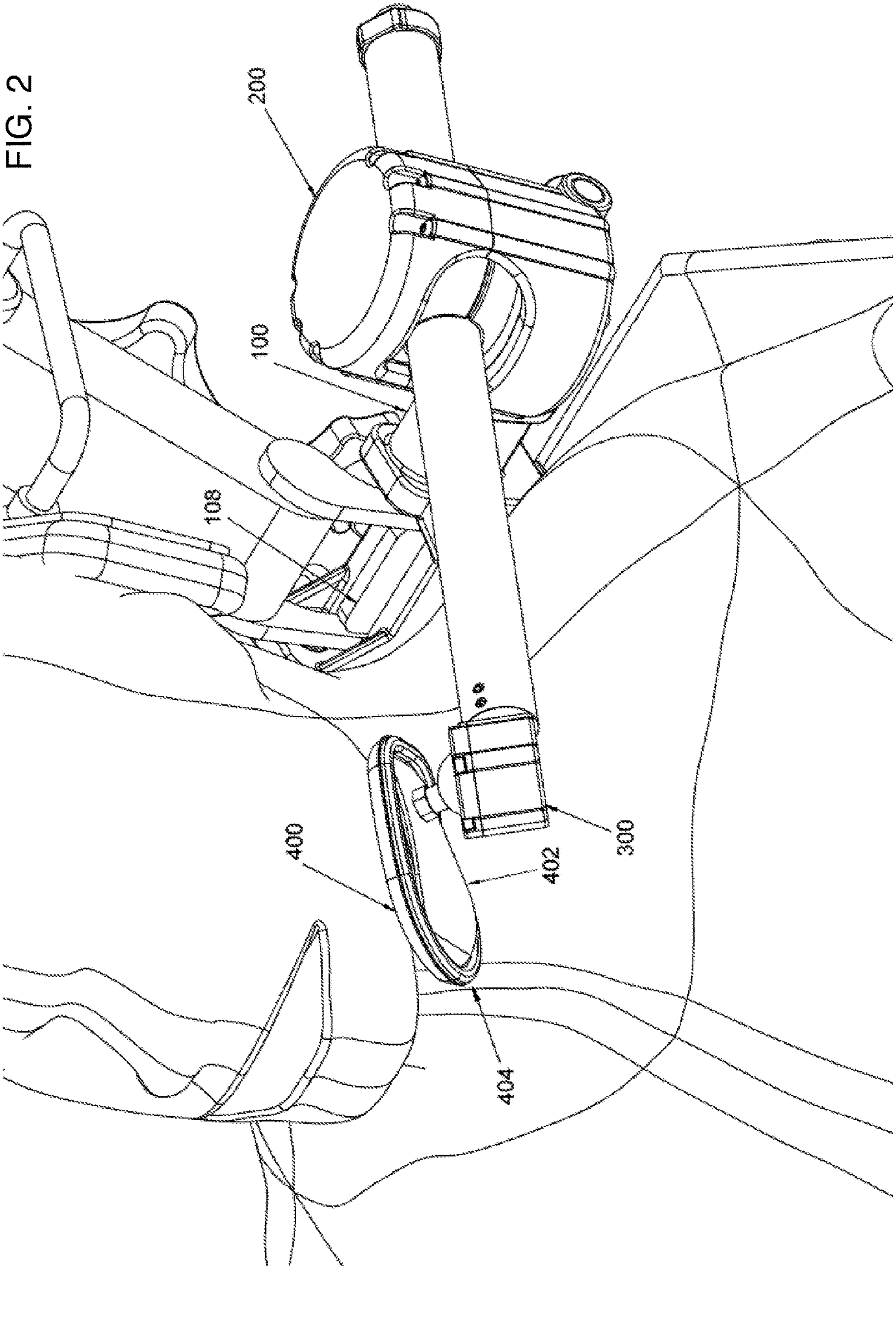
FIG. 2 is a perspective left side view of the disclosed jaw support device while in use.

In some embodiments, the jaw support device can include a headrest mount assembly 100, a split sphere assembly 200, a ball joint assembly 300, and a jaw rest assembly 400, as illustrated in FIGS. 1-2. Generally, the jaw support device can be configured to accurately support a patient's jaw using each of the four main assemblies 100, 200, 300, and 400. More specifically, the headrest mount assembly 100 can be used to configure the desired width of the device in relation to a patient's head, the split sphere assembly 200 can be used to finesse the width and height of the device in relation to a patient's head and to determine how far forward the device should be positioned for each patient, and the ball joint assembly 300 can position the jaw rest assembly 400 more specifically for each patient.

In some embodiments, the jaw rest assembly 400 also has flexibility to configure specifically to the contours of a patient's jaw. Once the device is placed in a desire position, activation of the device (for example, via air pressure or magnetism) can lock it in place. More specifically, in some cases, pneumatic air control, activation of a current in combination with a magnetorheological fluid can lock the split sphere assembly 200 and ball joint assembly 300 in place. Other fluids may be used instead of magnetorheological fluid. In some embodiments, air hoses can connect an air supply or air compressor to the split sphere assembly 200 and ball joint assembly 300. Generally, the air hoses can attach to the device using quick disconnect fittings, as described in more detail below. In other cases, wiring (such as in a power cord) can connect a power source to the spilt sphere assembly 200 and ball joint assembly 300.

The jaw support device can, via the headrest mount assembly 100, connect to the headrest stem 108 of a dental or other chair, as illustrated in FIG. 2. More specifically, the headrest mount assembly 100 may comprise a headrest mount center bridge 102, a width adjustor 104, an inner headrest mount tube 106, a width lock 110, and a center bridge knob 112. In some embodiments, the headrest mount assembly 100 may comprise, on an opposite side of the headrest stem 108, an additional width adjustor 104, inner headrest mount tube 106, and width lock 110 so the headrest mount assembly can support left and right split sphere assemblies 200, ball joint assemblies 300, and jaw rest assemblies 400, as illustrated in FIG. 1.

The headrest mount center bridge 102, as illustrated in FIGS. 1-2, can have a center aperture and the headrest stem 108 can be inserted through the top and bottom of the center bridge 102 and secured on the chair. More specifically, once the center bridge 102 is positioned on the headrest stem 108, the center bridge knob 112 can secure it. The center bridge knob 112 can be a knob, a toggle lock, or any other type of securing device that prevents the center bridge 102 and the rest of the jaw support device from unwanted movement during a procedure. For example, the center bridge knob 112 can have a threaded post coupled to a knob handle such that human manipulation of the knob handle causes the threaded post to move closer to a wedge plate that compresses against the headrest stem. Once the threaded post places an amount of pressure on the headrest stem that is great enough to hold the jaw support device in place, the device may be considered locked onto the chair.

Projecting out from one or each side of the center bridge 102, in some embodiments, can be a width adjustor 104 surrounding an inner headrest mount tube 106. A distal end of the inner headrest mount tube 106 can connect directly to the split sphere assembly 200 (for example, by a threaded portion) and can rotate when the split sphere assembly 200 is rotated.

The width adjustor 104 can expand and contract along a first axis to allow the split sphere assembly 200, ball joint assembly 300, and jaw rest assembly 400 to shift outward away from the center of the chair or inward toward the center of the chair. This feature allows for additional width adjustability and may be useful, for example, if an individual has broad or narrow shoulders.

When the jaw support device is to be stored or when a patient needs to get in and out of the chair, the user may wish to move the split sphere assembly 200, ball joint assembly 300, and jaw rest assembly 400 away from head region of the patient. Therefore, the user can rotate the split sphere assembly 200 backwards until the arm assemblies 200, 300, 400 are upright. In some embodiments, the headrest mount assembly may include a mechanism to prevent further rotation of the split sphere assembly 200 once the arm assemblies 200, 300, 400 are upright.

In some embodiments, each width adjustor 104 can include a width lock 110. Once the width adjustor 104 and inner headrest mount tube 106 are in a desired position, the width lock 110 can secure width adjustor and/or mount tube and, therefore, the position of split sphere assembly 200 in place. The width lock 110, as with the center bridge knob 112, can be a knob, a toggle lock, or any other type of securing device that prevents the split sphere assembly 200 from movement along the first axis or a second axis during a procedure.

Figure 10:
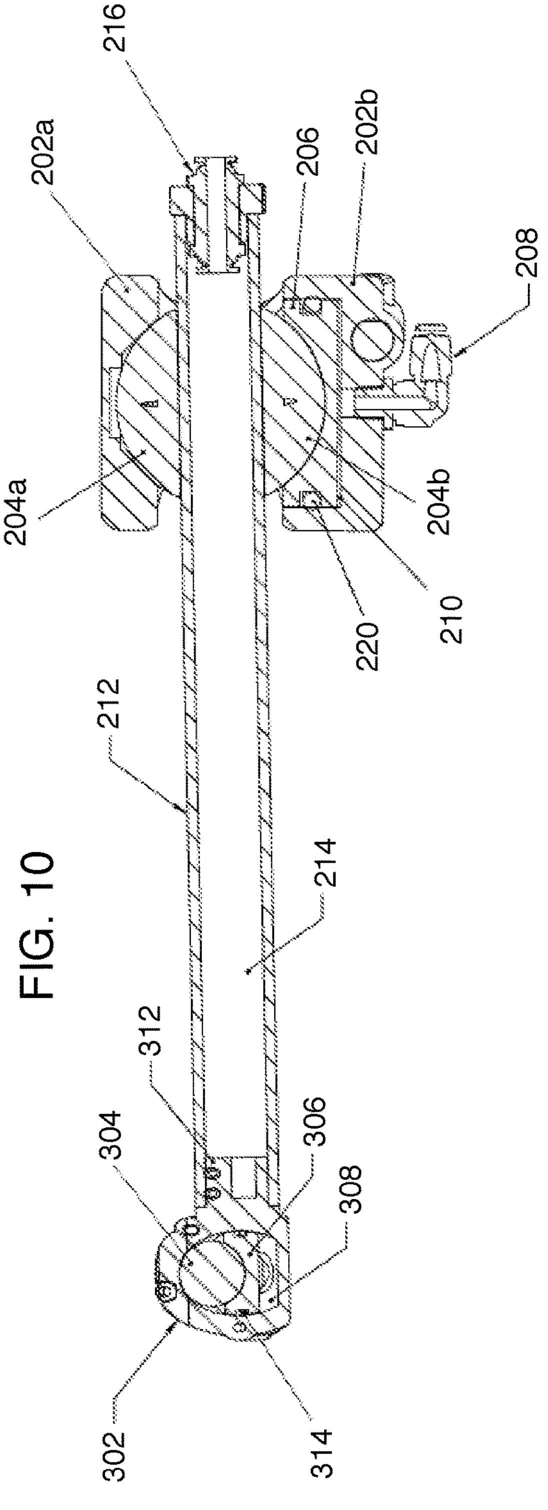
FIG. 10 is a cross-section view of the jaw support device of FIG. 5 shown from the line 10-10 in FIG. 9.
Figure 11:
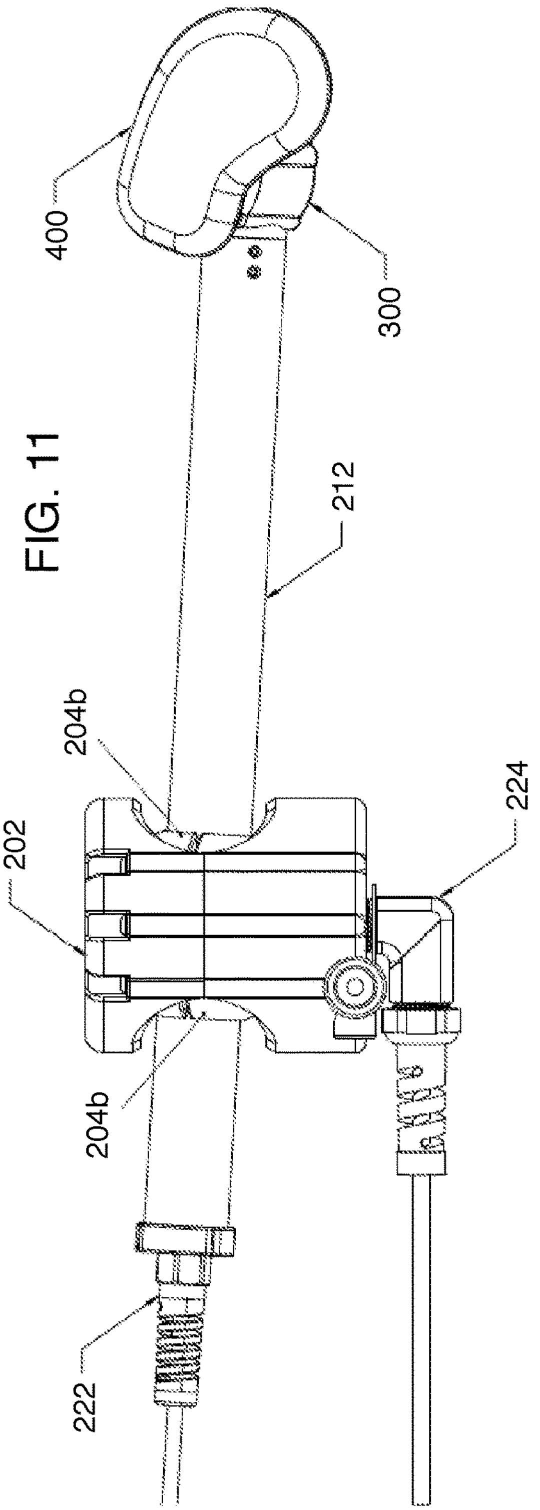
FIG. 11 is a side view of the split sphere assembly, ball joint assembly, and jaw rest assembly of one embodiment of the disclosed jaw support device.
Figure 12:
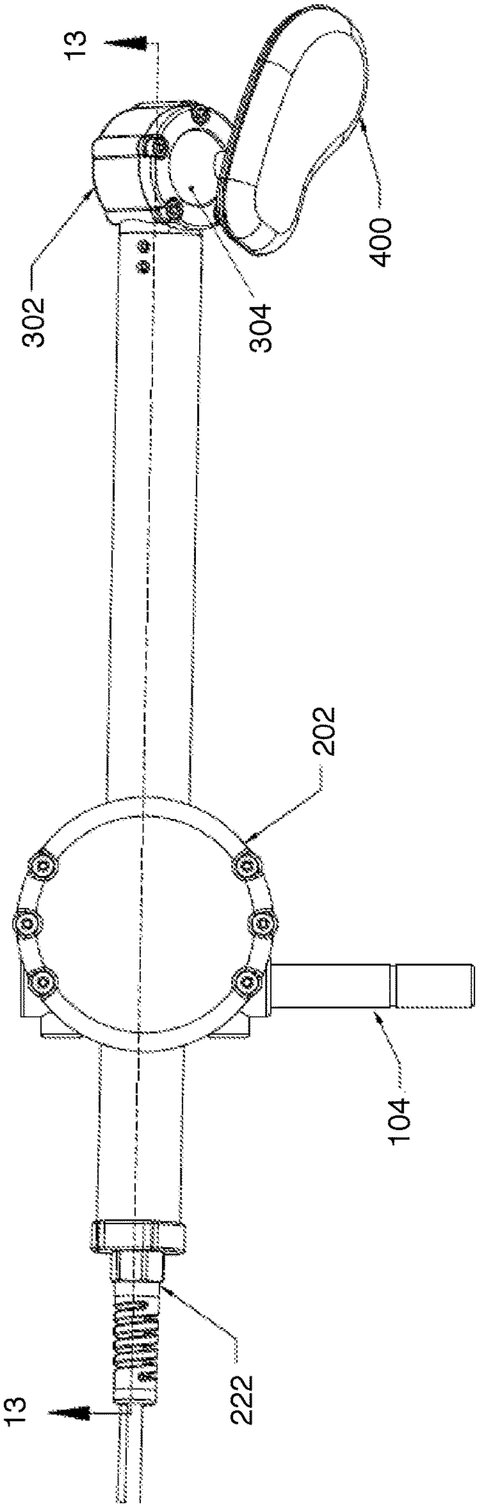
FIG. 12 is a top plan view of the jaw support device of FIG. 11.
Figure 13:
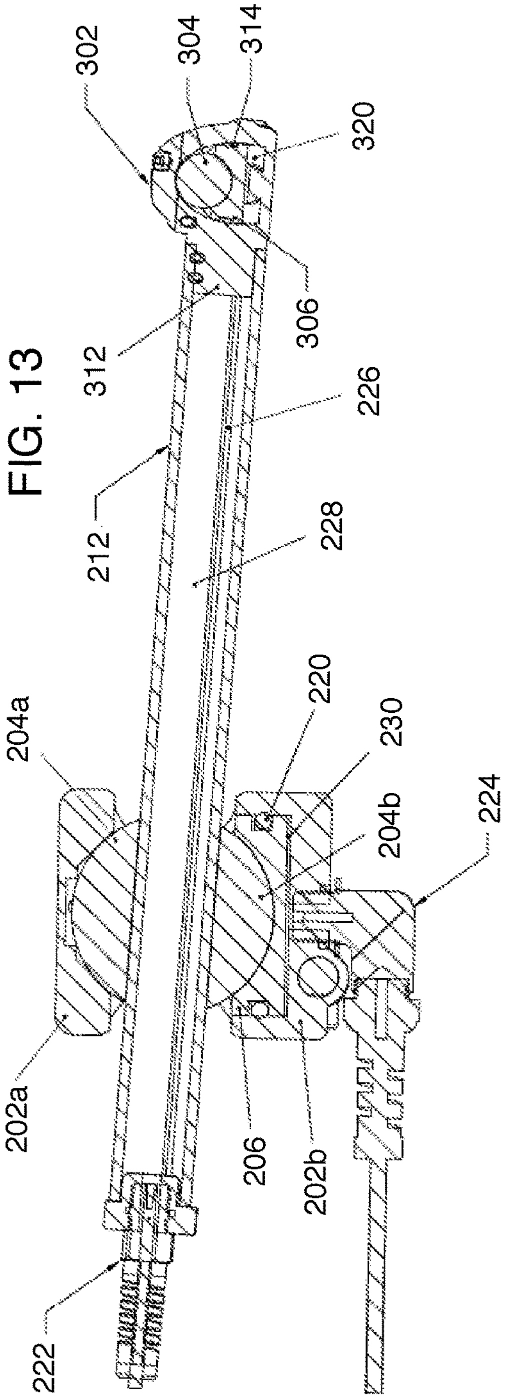
FIG. 13 is a cross-section view of the jaw support device of FIG. 11 shown from the line 13-13 in FIG. 12.

In some embodiments involving a pneumatic air locking mechanism, and as illustrated in FIGS. 3 and 5-10, the split sphere assembly 200 may comprise a split sphere housing 202 having an upper portion 202*a* and a lower portion 202*b*, a split sphere ball 204, a split sphere piston 206, a split sphere air valve 208, a split sphere housing air cavity 210, an arm extension including a hollow tube arm 212 and a tube arm hose 214, and a ball joint air valve 216. In other embodiments involving an electric locking mechanism, and as illustrated in FIGS. 11-13, the split sphere assembly 200 may comprise a split sphere housing 202 having an upper portion 202*a* and a lower portion 202*b*, a split sphere ball 204, a split sphere piston 206, a split sphere electrical connection 224, a split sphere housing fluid cavity 230 where the magnetorheological fluid can be stored, an arm extension including a hollow tube arm 212 having wiring 226 within a cavity 228, and a ball joint electrical connection 222. As mentioned above, the split sphere assembly 200 can be used to finesse the width and height of the device and to determine how far forward the device should be positioned for each patient.

Figure 5:
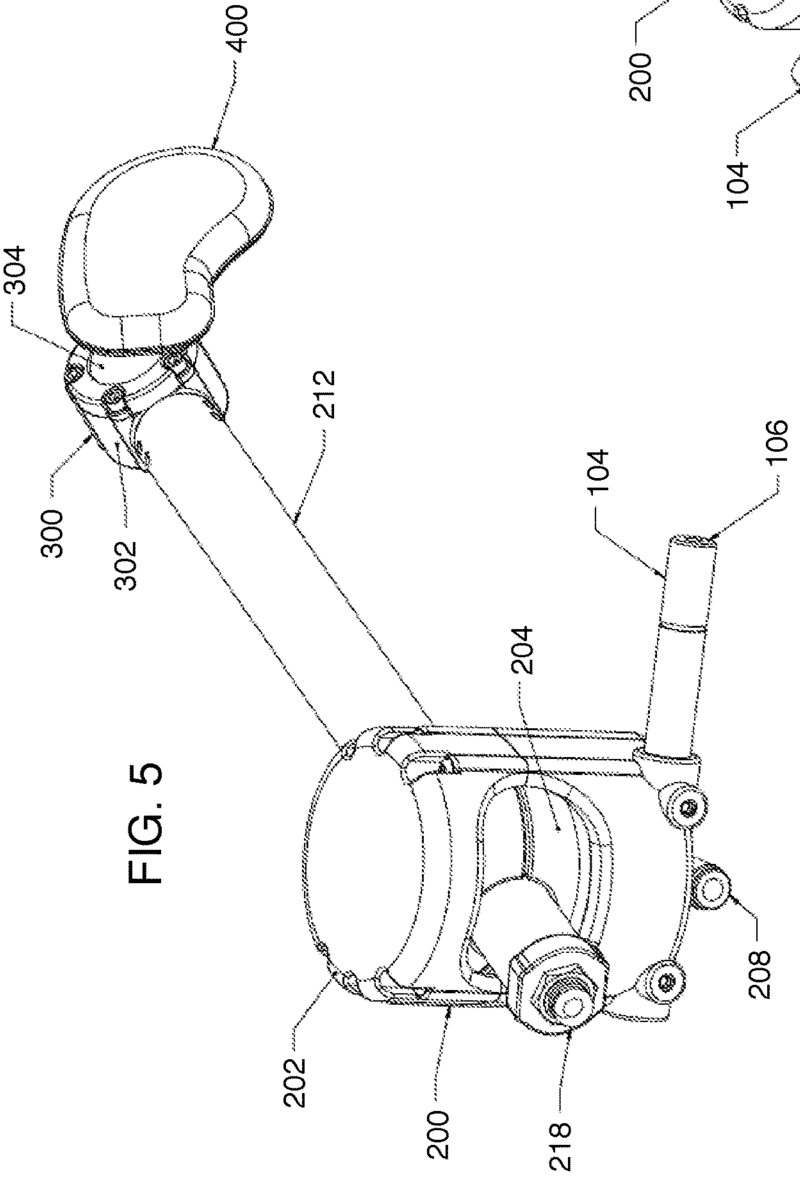
FIG. 5 is perspective back inner view of the split sphere assembly, ball joint assembly, and jaw rest assembly of one embodiment of the disclosed jaw support device.

The split sphere housing 202 can operate as the home base of the split sphere assembly 200 and can, in effect, connect the headrest mount assembly 100 to the ball joint assembly 300. More specifically, the inner headrest mount tube 106 can connect directly to the outer surface of the split sphere housing 202, the split sphere housing 202 can contain the split sphere ball 204, and the hollow tube arm 212 and tube arm hose 214 can fit through the front of the split sphere housing 202 and through the central cavity of the split sphere ball 204 and can connect on a distal end to the ball joint assembly 300, as illustrated in FIG. 5.

The split sphere housing 202 can be roughly cylindrical, wherein the top and bottom outer faces are relatively flat and wherein the front and back facing portions of the curved part of the housing 202 each include a wide aperture. When rotated, as described above, the bottom and top of the split sphere housing 202 can face forward and backward, respectively, the front wide aperture can face upward, and the back wide aperture can face downward relative to the dental chair, as illustrated in FIG. 1.

Attached to an outer portion of the split sphere housing 202, in addition to the inner headrest mount tube 106, can be the split sphere air valve 208 or split sphere electrical connection 224. The inner headrest mount tube 106 can attach on the inward facing outer curved surface of the split sphere housing 202, as illustrated in FIG. 1. The split sphere air valve 208 or split sphere electrical connection 224 can attach on the bottom outer face of the split sphere housing 202, as illustrated in FIGS. 10 and 13. In some cases, a first end of additional tubing can attach to the split sphere air valve 208 and a second end of this additional tubing can attach to either the air supply in the room or to a free-standing air compressor positioned near the chair. In the case of a magnetic locking mechanism, a first end of a power cord can attach to the split sphere electrical connection 224 and a second end of the power cord can attach to a power supply, such as an outlet, battery, or generator.

Figure 3:
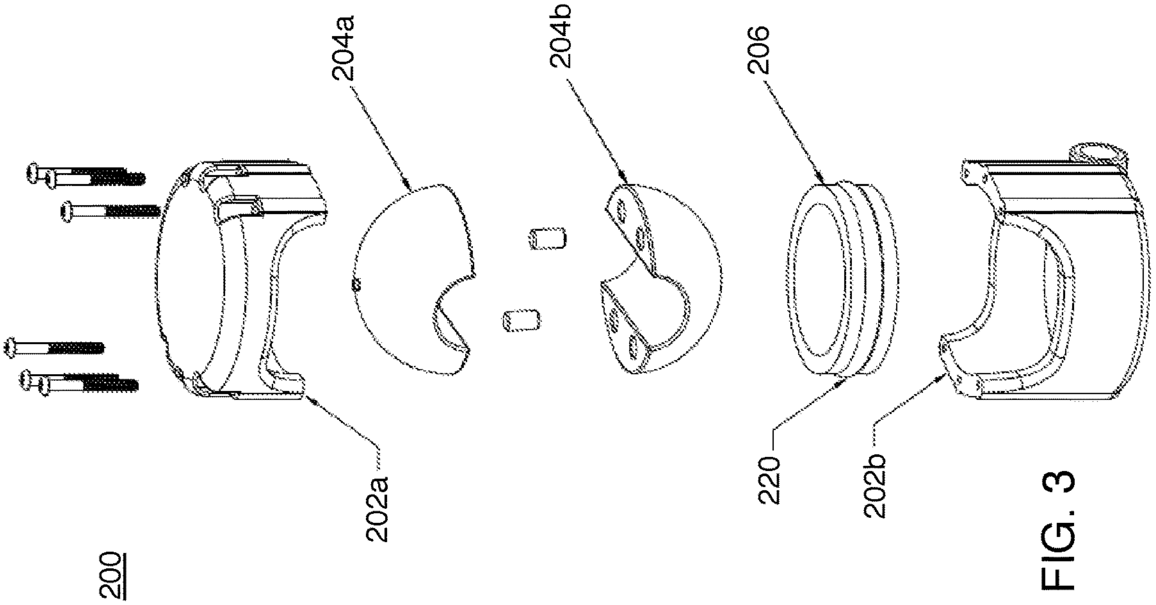
FIG. 3 is an exploded view of the housing and interior components of the split sphere assembly of the disclosed jaw support device.

The split sphere ball 204, which can be located within the split sphere housing 202, is roughly spherical and includes an upper half 204*a* and a lower half 204*b* that are each dome-shaped as well as a cylindrical aperture through its center, wherein half of the aperture is carved out of the domed upper half and half of the aperture is carved out of the domed lower half, as illustrated in FIG. 3. When in use, the cylindrical aperture can align with, and face out from, the front and back wide apertures of the split sphere housing 202, as illustrated in FIGS. 1-2. In some embodiments, the upper half 204*a* and lower half 204*b* of the split sphere ball 204 have flexibility to move away from and toward each other, thereby applying various amounts of pressure to the hollow tube arm 212, which fits therebetween, as illustrated in FIG. 2.

The split sphere piston 206, which can be located within the split sphere housing 202 and beneath the split sphere ball 204, as illustrated in FIGS. 3, 10 and 13, can be roughly cylindrical with a cavity around the central circumference of the outer surface of the split sphere piston. The centrally located cavity can create upper and lower lips for the split sphere piston 206 and can house an O-ring 220, as illustrated in FIG. 3, which can, for example, create a secure air seal that prevents air leakage within the split sphere housing 202.

Beneath the split sphere piston 206, and within the split sphere housing 202, can be a split sphere housing air cavity 210, as illustrated in FIG. 10. This air cavity 210 can also have an opening through the bottom of the lower portion 202*b* of the split sphere housing 202 into which the split sphere air valve 208 can fit. As described above, the split sphere air valve 208 can attach on the bottom outer face of the lower portion 202*b*. The air valve 208 can include a right-angle bend and can be a push-to-connect fitting, a hose barb, or any other form of air valve.

When the air valve 208 is activated, it creates air pressure in the air cavity 210, which causes the split sphere piston 206 to press upward against the split sphere ball 204. Since the upper and lower halves of the split sphere ball 204, as described above, have flexibility to move away from and toward each other, activation of the air valve 208 and the corresponding movement of the split sphere piston 206 upward so that it makes contact with, and pushes on, the split sphere ball 204 causes the bottom half 204*a* of the split sphere ball to move toward the upper half 204*a*. The upper half 204*a* then moves upward until it makes contact with the inner surface of the top of the split sphere housing 202 and cannot move any further. Once both halves of the split sphere ball 204 have moved upward as much as possible, they in effect, pinch the hollow tube arm 212 between them and lock it in place.

In some embodiments, the lower portion 202*b* of the split sphere housing 202 can include a split sphere housing fluid cavity 230, as illustrated in FIG. 13, where the magneto-rheological fluid can be stored. This fluid cavity 230, similar to the air cavity 210, can also have an opening through the lower portion 202*b* into which the split sphere electrical connection 224 can fit. Similar to the split sphere air valve 208, the split sphere electrical connection 224 can attach on the bottom outer face of the lower portion 202*b*. The electrical connection 224 can also include a right-angle bend, as illustrated in FIG. 11.

Similar to the air activated locking mechanism, when the magnetic locking mechanism is activated, it causes the magnetorheological fluid to increase in viscosity to become a viscoelastic solid, which causes the split sphere ball 204 to be held in place. By essentially freezing the split sphere ball 204 in place, the split sphere ball causes the hollow tube arm 212 to be locked in place.

Figure 4:
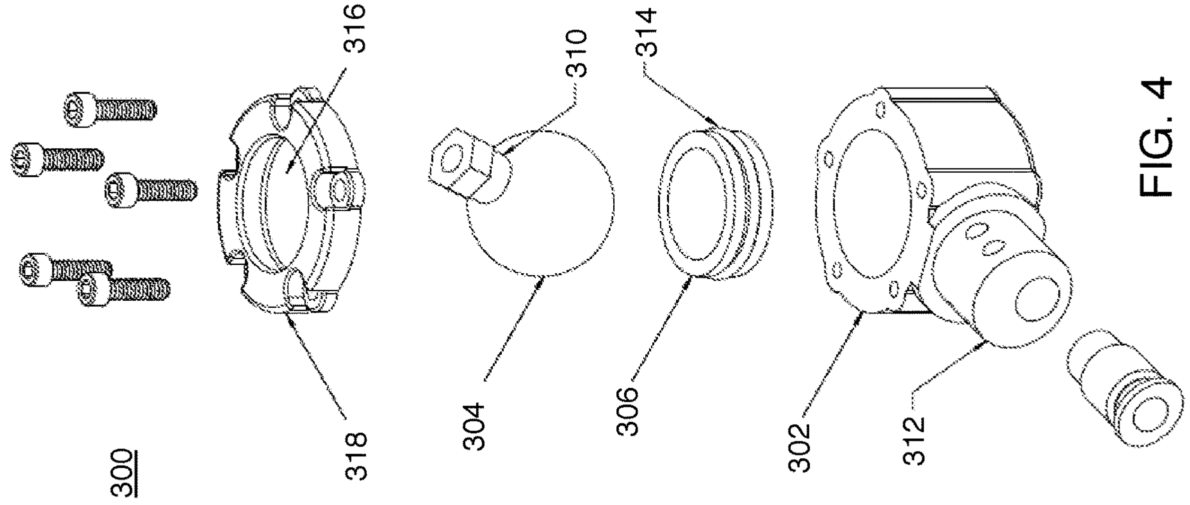
FIG. 4 is an exploded view of the ball joint assembly of the disclosed jaw support device.

The hollow tube arm 212 can be a cylindrical, hollow tube that, as briefly described above, connects the split sphere assembly 200 to the ball joint assembly 300. More specifically, a portion of the hollow tube arm 212 can be located within the cylindrical aperture of the split sphere ball 204, as illustrated in FIG. 4, and the distal end of the hollow tube arm 212 can connect to the ball joint assembly 300, as illustrated in FIGS. 1 and 5-13.

The hollow tube arm 212 can be of a length suitable to reach the front of a patient's face. However, the length of the hollow tube arm in relation to the front of the patient's face can be adjustable. For example, the hollow tube arm 212, in some embodiments, may be able to slide back and forth through the cylindrical aperture of the split sphere ball 204. This enables the device to accommodate variations in the size of patients' bodies and also enables the device to tuck away along the dental chair when no longer needed, as illustrated in FIG. 1.

The tube arm hose 214, similar to the hollow tube arm 212, can be a cylindrical, hollow tube. It may be located within the hollow tube arm 212, as illustrated in FIG. 10, and is approximately the same length as the hollow tube arm 212. In some embodiments, the tube arm hose 214 connects on its proximal end to the ball joint air valve 216 and on its distal end to the ball joint housing 302.

The ball joint air valve 216, similar to the split sphere air valve 208, can be a push-to-connect fitting, a hose barb, or any other form of air valve. In some embodiments, the ball joint air valve 216 acts as a plug at the proximal end of the tube arm hose 214 and, therefore, prevents air from escaping the tube arm hose 214. Further, the ball joint air valve 216 can also operate as a stop to prevent the tube arm hose 214 from sliding out of the split sphere ball 204 in its entirety. Alternatively, a separate stopper can be used for the hollow tube arm 212 that has a hole through its center to accommodate the tube arm hose 214 and ball joint air valve 216. As with the split sphere air valve 208, a first end of additional tubing can attach to the ball joint air valve 216 and a second end of this additional tubing can attach to either the air supply in the room or to a free-standing air compressor or tank positioned near the chair.

Instead of a tube arm hose 214, the hollow tube arm 212 may have wiring 226 within a cavity 228 of the hollow tube arm, as illustrated in FIG. 13. The wiring 226 may be approximately the same length as the hollow tube arm 212. In some embodiments, the wiring 226 can connect on its proximal end to the ball joint electrical connection 222 and on its distal end to the ball joint housing 302. The ball joint electrical connection 222 may further connect to a power cord having a connection to a power supply.

Therefore, similar to the split sphere electrical connection 224, a first end of a power cord can attach to the ball joint electrical connection 222 and a second end of the power cord can attach to a power supply. In some embodiments, the ball joint electrical connection 222 acts as a plug at the proximal end of the tube arm hose 214. Further, the ball joint electrical connection 222 can also operate as a stop to prevent the wiring 226 from sliding out of the split sphere ball 204 in its entirety. Alternatively, a separate stopper can be used for the hollow tube arm 212 that has a hole through its center to accommodate the wiring 226 and ball joint electrical connection 222.

In some embodiments involving a pneumatic air locking mechanism, and as illustrated in FIGS. 4-10, the ball joint assembly 300 may comprise a ball joint housing 302, a ball joint ball 304, a ball joint piston 306, a ball joint housing air cavity 308, a ball joint rod 310, and a tube arm connector 312. In other embodiments that involve a magnetic locking mechanism, and as illustrated in FIGS. 11-13, the ball joint assembly 300 may comprise a ball joint housing 302, a ball joint ball 304, a ball joint piston 306, a ball joint housing fluid cavity 320 where the magnetorheological fluid can be stored, a ball joint rod 310, and a tube arm connector 312. As mentioned above, the ball joint assembly 300 can be used to position the jaw rest assembly 400 more specifically to each patient's jaw.

Figure 6:
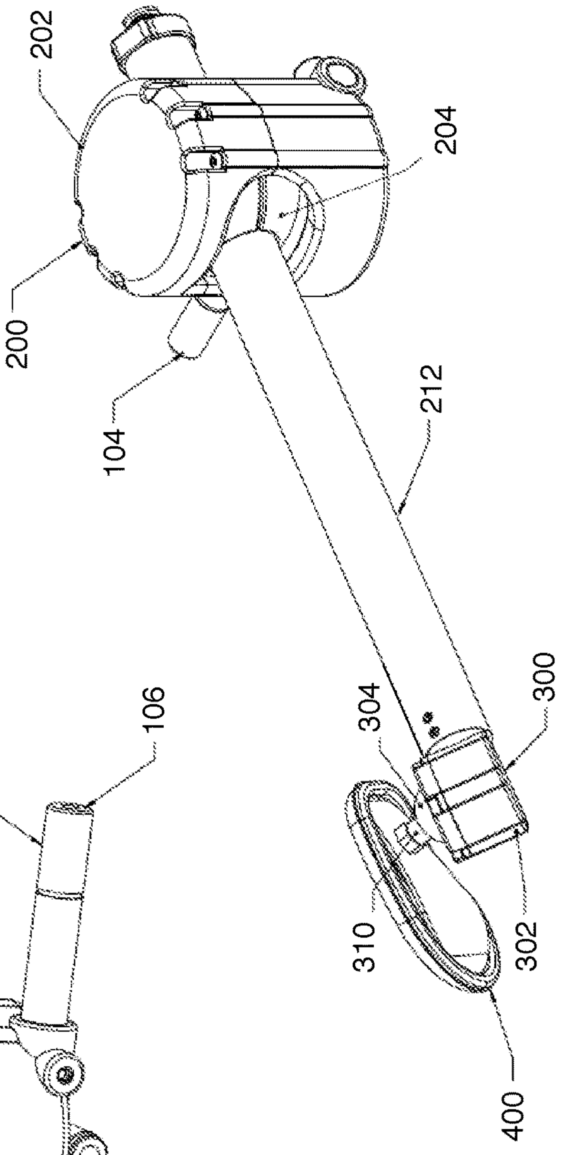
FIG. 6 is a perspective front outer view of the disclosed jaw support device of FIG. 5.

The ball joint housing 302 can operate as the home base of the ball joint assembly 300 and can connect the split sphere assembly 200 to the jaw rest assembly 400. More specifically, the hollow tube arm 212 and the tube arm hose 214 or wiring 226 can attach to the ball joint housing 302 (for example, at an outer surface of the housing), the ball joint housing 302 can contain the ball joint ball 304, and the ball joint rod 310 can attach to the ball joint ball 304 on its proximal end and to the jaw rest assembly 400 on its distal end, as illustrated in FIG. 6.

The ball joint housing 302 can be roughly cylindrical, wherein the inner and outer faces are relatively flat and wherein at least one of the relatively flat faces of the housing 302 includes an aperture 316. The aperture can, in some cases, be circular, as illustrated in FIG. 4. In some embodiments, the ball joint housing 302 may include a ball joint housing cover 318 to enable assembly and disassembly of the ball joint assembly 300. As illustrated in FIGS. 4, 10 and 13, the ball joint housing 302 may include a tube arm connector 312 on its curved outer surface with which the hollow tube arm 212 and tube arm hose 214 or wiring 226 can couple. Therefore, in some embodiments, when the hollow tube arm 212 and the tube arm hose 214 or wiring 226 rotate or spin around their central rotation axis, the inner and outer faces of the ball joint housing 302 can rotate accordingly to face directions corresponding to the degrees and direction of rotation. In other embodiments, the hollow tube arm 212 is not securely connected to the ball joint housing 302 and, therefore, does not directly cause the ball joint housing 302 to rotate. For example, the tube arm hose 214 or wiring 226 may securely connect to the ball joint housing 302 but rotate freely compared to the hollow tube arm 212.

The ball joint ball 304, which can be located within the ball joint housing 302, is spherical in some embodiments (it may also be conical or ellipsoidal), and at least a portion of the ball joint ball 304 can protrude out from the aperture 316 of the ball joint housing 302. However, at least one portion of the opening of the aperture 316 in the ball joint housing 302 is smaller than at least one cross-section portion of the ball joint ball 304 and, therefore, the ball joint ball 304 can remain securely contained within the ball joint housing 302. For example, if the ball joint ball 304 is a sphere, at least its diameter will be wider than a portion of the aperture 316.

The ball joint piston 306, which can be located within the ball joint housing 302 and on the side of the ball joint ball 304 opposite the aperture 316, as illustrated in FIGS. 4, 10 and 13, can be roughly cylindrical with a cavity around the central circumference and a flat top face and a flat bottom face. The centrally located cavity can create upper and lower lips for the ball joint piston 306 and can house an O-ring 314, which can, for example, create a secure air seal that prevents air leakage out of the ball joint housing 302. In some embodiments, the ball joint ball 304 and ball joint piston 306 have extra space within the ball joint housing 302 in which to move. This allows a user to rotate the ball joint ball 304 into a desired position.

Located between the ball joint piston 306 and relatively flat outer facing portion of the ball joint housing 302 can be a ball joint housing air cavity 308, as illustrated in FIG. 10. This air cavity 308 can be open to the connection point of the tube arm hose 214 on the side of the ball joint housing 302. Therefore, air pressure changes within the ball joint housing 302 can take place initially in the ball joint housing air cavity 308.

More specifically, when the ball joint air valve 216 at the proximal end of the tube arm hose 214 is activated, it can create air pressure in the air cavity 308, which causes the ball joint piston 306 to press upward toward the ball joint ball 304 so that a flat face of the ball joint piston is in contact with the ball joint ball. Since the ball joint ball 304 and ball joint piston 306, as described above, have extra space within the housing 302, activation of the air valve 216 and the corresponding movement of the ball joint piston 306 in the direction of the ball joint ball so that the ball joint piston and ball joint ball are in contact causes the ball joint ball 304 to move toward the aperture 316 until it is pressed against the inner face of the ball joint housing 302. Since the inner face of the ball joint housing 302 defines the outer boundary of the aperture 316, when the ball joint ball makes contact with the inner face of the ball joint housing and is also in contact with the ball joint piston 306, it is, therefore, in a locked position and causes the ball joint rod 310 to be locked in place.

In some embodiments when the magnetic locking mechanism is used, the ball joint housing 302 can include a ball joint housing fluid cavity 320, as illustrated in FIG. 13, where the magnetorheological fluid can be stored. This fluid cavity 320, similar to the air cavity 308, can also be open to the connection point of the wiring 226 on the side of the ball joint housing 302. Therefore, activation of the magnetorheological fluid within the ball joint housing 302 can take place in the ball joint housing fluid cavity 320.

More specifically, when the ball joint electrical connection 222 at the proximal end of the wiring 226 is activated, it can cause the magnetorheological fluid to increase in viscosity, which causes the ball joint ball 304 to be held in place. By essentially freezing the ball joint ball 304 in place, the ball joint ball causes the ball joint rod 310 to also be locked in place.

The ball joint rod 310 can be a short, cylindrical tube that, as briefly described above, connects the ball joint assembly 300 to the jaw rest assembly 400. More specifically, a proximal end of the ball joint rod 310 can be attached to, or a part of, the ball joint ball 304, as illustrated in FIGS. 4 and 6, and the distal end of the ball joint rod 310 can connect to the jaw rest assembly 400, as illustrated in FIG. 6. This connection can be, for example, between a threaded post protruding from the underside of the jaw rest assembly 400 and a bolt on the end of the ball joint rod 310, as illustrated in FIG. 4.

Figure 15:
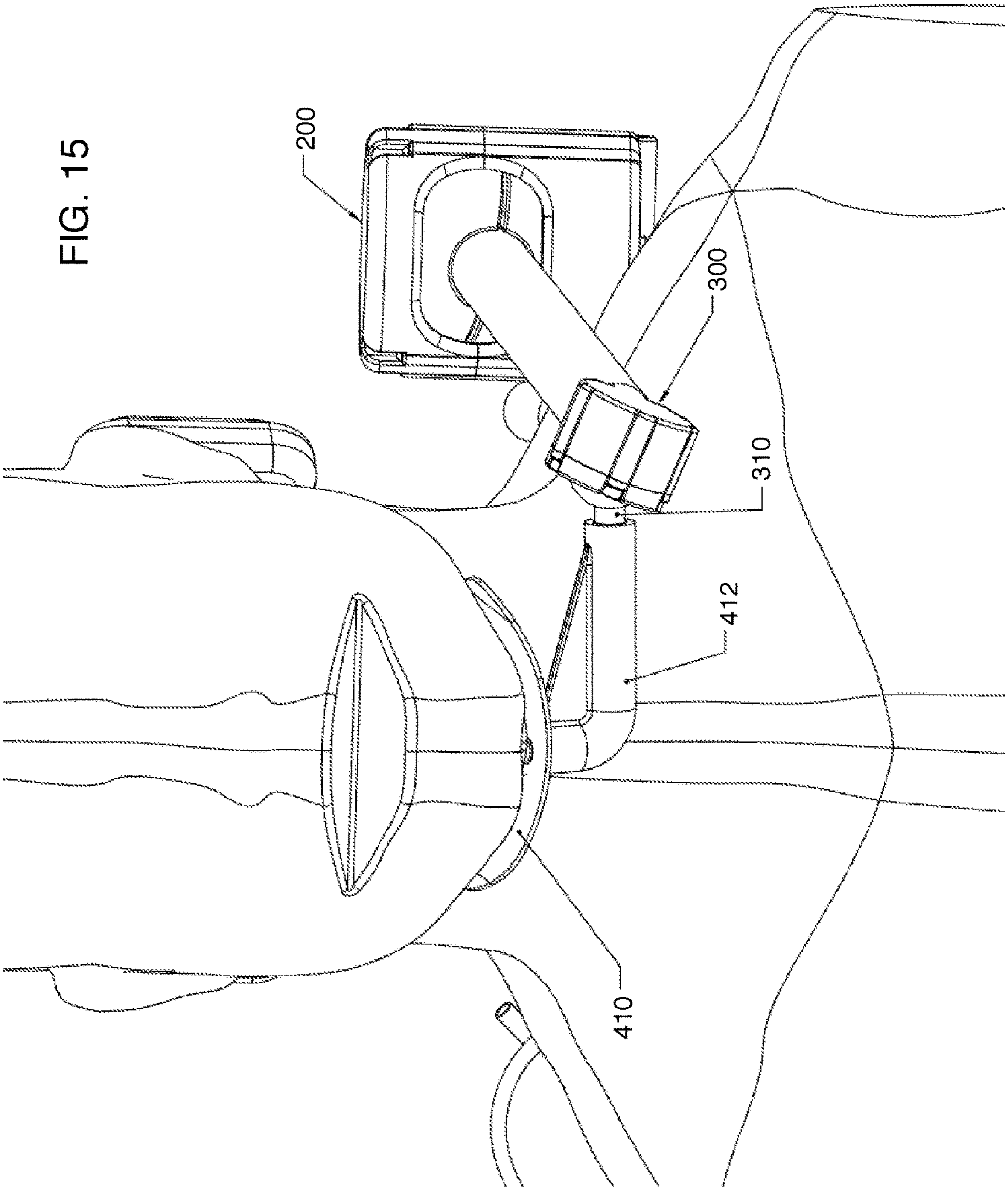
FIG. 15 is front view of one embodiment of the disclosed jaw support device while in use.
Figure 16:
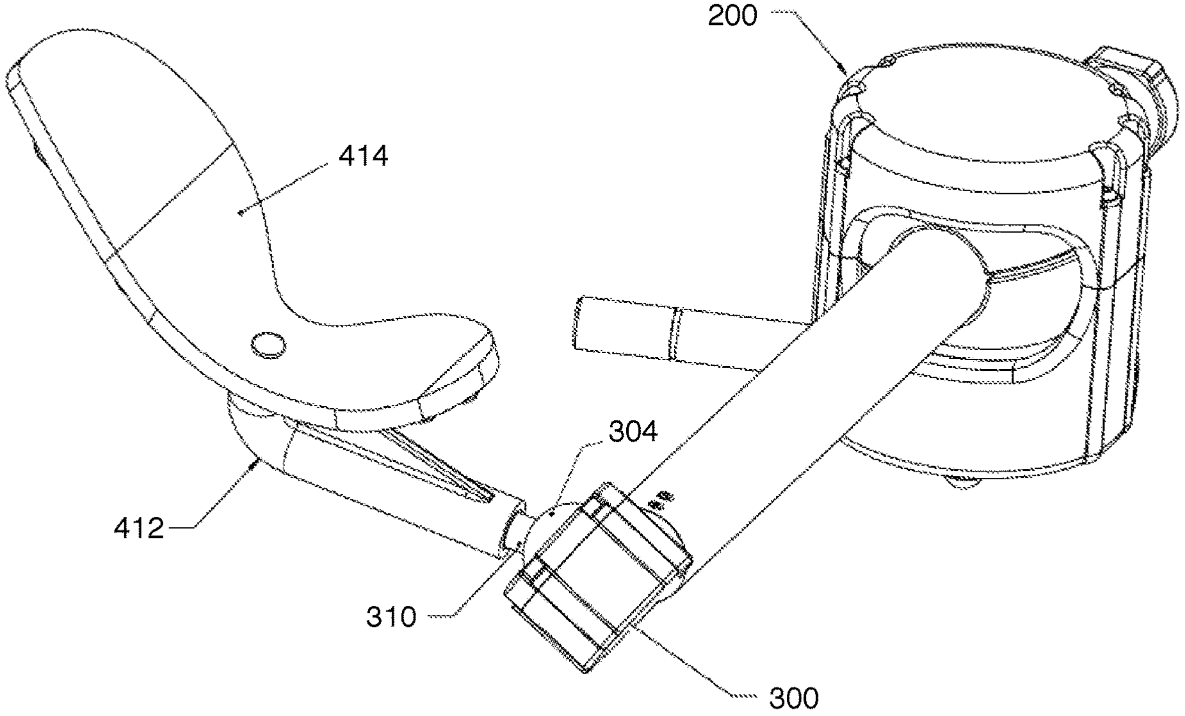
FIG. 16 is perspective front view of a split sphere assembly, ball joint assembly, and jaw rest assembly of one embodiment of the disclosed jaw support device.
Figure 17:
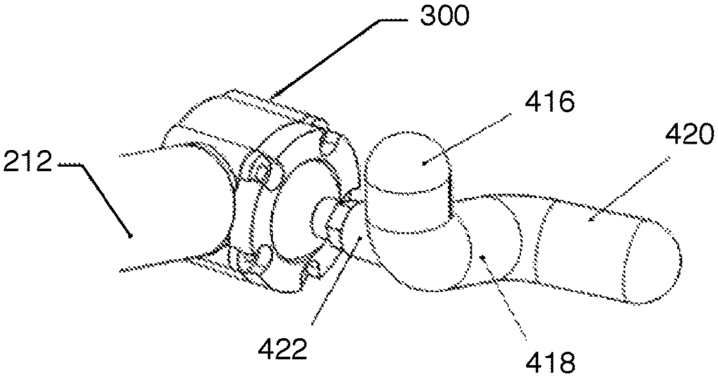
FIG. 17 is a perspective back view of the ball joint assembly of one embodiment of the disclosed jaw support device.

In some embodiments, as illustrated in FIGS. 6-9 and 11-12, the jaw rest assembly 400 may comprise a jaw rest connector 404 and one or more jaw rests, such as a bilateral jaw rest 402. In a second embodiment, as illustrated in FIG. 15, the jaw rest assembly 400 may comprise a jaw rest connector 412 and a jaw rest 410 that is positioned under the front part of the jaw (i.e., chin). In a third embodiment, as illustrated in FIG. 16, the jaw rest assembly 400 may comprise the jaw rest connector 412 and one or more jaw rests, such as a unilateral jaw rest 414. In a fourth embodiment, as illustrated in FIG. 17, the jaw rest assembly 400 may include a jaw rest comprising a vertical support 416, a horizontal support 418, and a jaw rest 420 as well as a jaw rest connector 422. The jaw rest assembly 400 can be manipulated to create an optimal fit regardless of the curvature of each patient's jaw.

Figure 7:
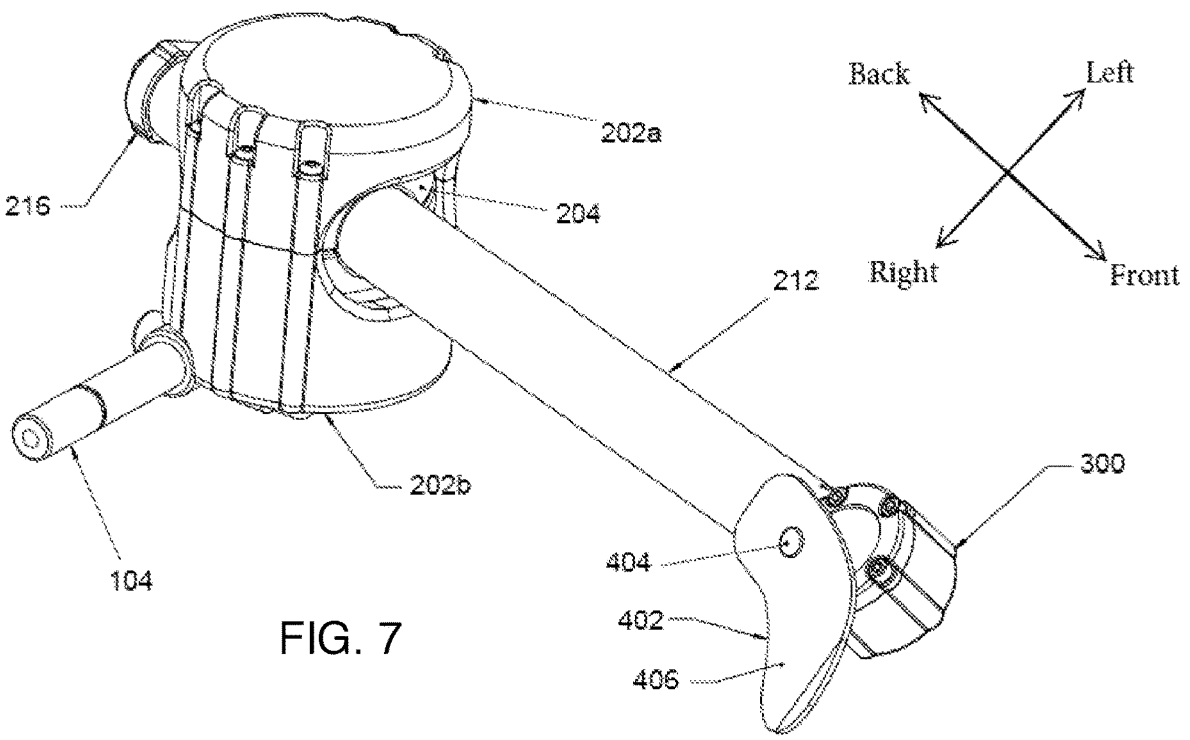
FIG. 7 is a perspective front inner view of the jaw support device of FIG. 5 showing the main body of the jaw rest with no padded surface attached.
Figure 8:
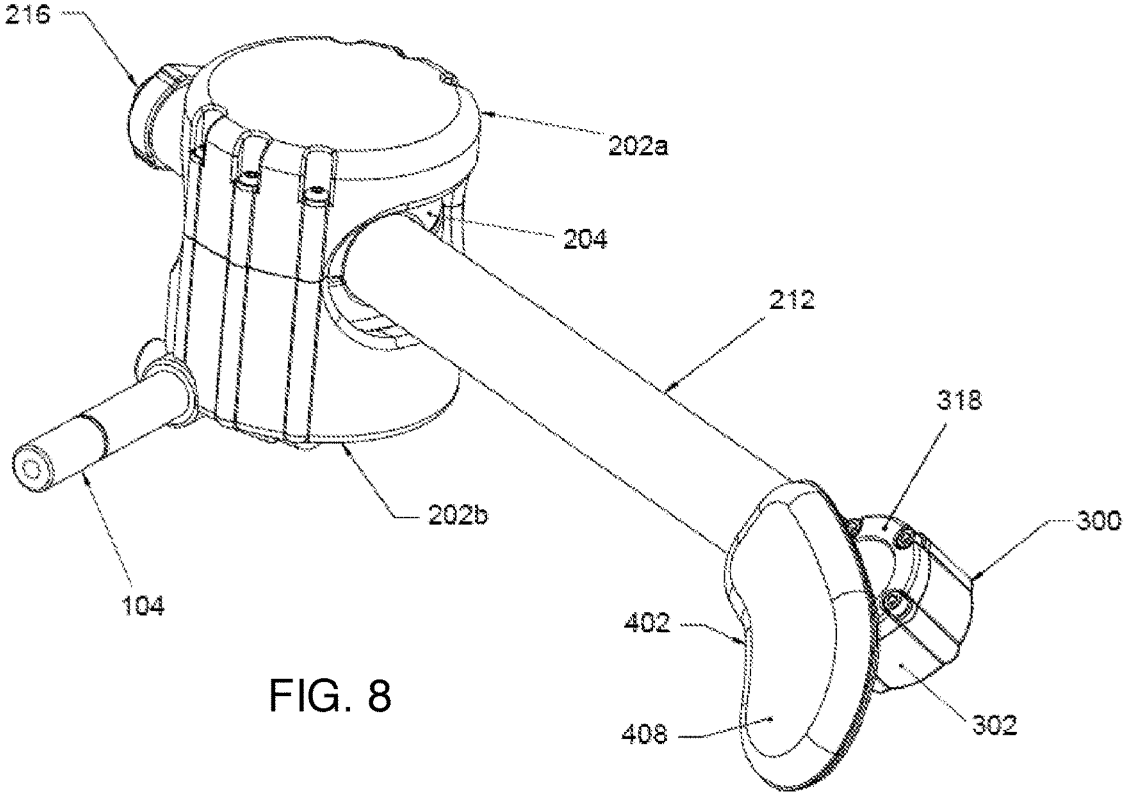
FIG. 8 is a perspective front inner view of the jaw support device of FIG. 5 showing the main body of the jaw rest with a padded surface attached.
Figure 9:
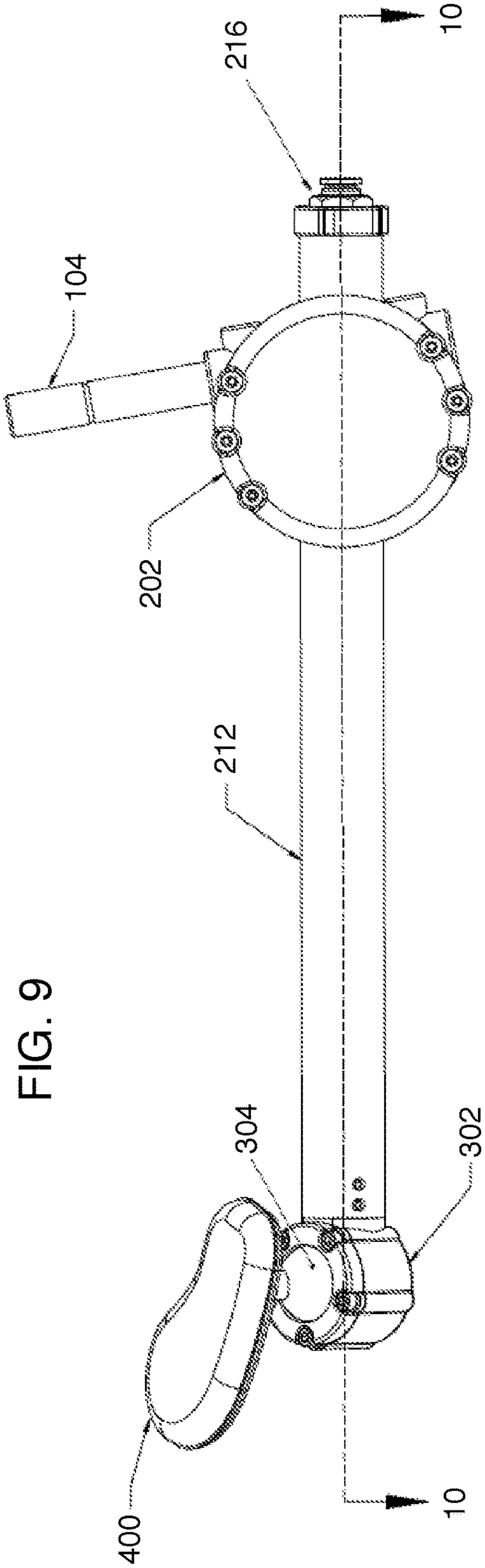
FIG. 9 is a top plan view of the jaw support device of FIG. 5.

As described above, the jaw rest connector 404, 412, 422 and the ball joint rod 310 can be joined together to connect the ball joint assembly 300 to the jaw rest assembly 400. More specifically, in some embodiments, as illustrated in FIGS. 6-7 and 17, the jaw rest connector 404 can attach to the ball joint rod 310. For example, the jaw rest connector 404 can be a short, fully or partially threaded post that can fit in the ball joint rod 310 and can be secured thereto using a variety of means (for example, a hex nut). The use of a connector on each assembly 300, 400 enables a user to switch out different variations of the jaw rest assembly 400 depending on the patient's needs.

A first embodiment of the jaw rest assembly 400, illustrated in FIGS. 1-2, 5-9, and 11-12, can include one or more bilateral jaw rests 402, wherein each bilateral jaw rest is comprised of, for example, a metal or plastic frame and attached to a jaw rest connector 404, and wherein each bilateral jaw rest 402 can be flat or curved. One embodiment of a curved bilateral jaw rest 402 is illustrated in FIGS. 2 and 5-6. The bilateral jaw rest 402 may be structured and configured to include a wide, smooth main body 406 comprised of a rigid frame (for example, metal or plastic), as illustrated in FIG. 7. The jaw rest connector 404 can be an elongated rod that has a first end connected to the ball joint assembly and a second end connected to the main body 406.

A padded surface 408 may attach to and/or cover at least one side (for example, the top) of the smooth main body 406 for a side of the patient's jaw to rest on, as illustrated in FIGS. 2, 5-6, 8-9, and 11-12. If two bilateral jaw rests 402 are used, one can be used on each side of the patient's jaw by attaching to each of the ball joint assemblies 300 and, therefore, the left and the right side of the jaw can be supported by the jaw support device. In some use cases, the bilateral jaw rest 402 can be implemented on a first side of the patient, and a different embodiment of the jaw rest assembly 400 having, for example, a jaw rest 410 can be implemented on a second side of the patient to accurately and thoroughly support the patients' jaw.

A second embodiment of the jaw rest assembly 400, illustrated in FIG. 15, can include a jaw rest 410 attached to the jaw rest connector 412. This version of the jaw rest provides broad support by being positioned under the front part of the jaw (i.e., the chin). The jaw rest 410 can include a wide and slightly curved main body comprised of, for example, a metal or plastic frame and a padded surface for the patient's chin to rest on. The jaw rest connector 412 can be comprised of a horizontal and a vertical portion, or component, connected on their ends so as to create a 90-degree angle between the two portions. The jaw rest 410 can connect on the top or first end of the vertical portion and the horizontal portion can connect on the bottom or second end of the vertical portion, as illustrated in FIG. 15, and allows for the patient's jaw to be rotated side to side. As with the first embodiment, the jaw support device can have two sides and, therefore, in some embodiments, the second embodiment of the jaw rest assembly 400 having the jaw rest 410 connected to the jaw rest connector 412 can be implemented on a first side of the patient, and a different embodiment of the jaw rest assembly 400 having, for example, the bilateral jaw rest 402 can be implemented on a second side of the patient.

A third embodiment of the jaw rest assembly 400, illustrated in FIG. 16, can include a unilateral jaw rest 414 attached to the jaw rest connector 412. This version provides support to a patient when the patient's head is tilted to one side during a procedure. More specifically, the unilateral jaw rest 414 may be structured and configured to offer curvature around a patient's jaw, similar to the jaw rest 410, but to have one side more elongated than the other. For example, the unilateral jaw rest 414 can include a wide and slightly curved main body and an elongated side section, wherein the main body and side section can both be comprised of a metal or plastic frame and include a padded surface for the patient's jaw to rest on. This design is useful because it cups a patient's jaw more completely than the jaw rest 410, thereby allowing for a more extreme tilt of a patient's head to better access difficult-to-reach portions of a patient's mouth.

Therefore, if a user would like to tilt the patient's head to the right side during a procedure (for example, because the user is left-handed and needs to rotate the patient further to the right side to access the third molar tooth), the user can help support the patient's jaw on the right side with the device by attaching the jaw rest assembly 400 to the right side ball joint assembly 300, which positions the longer side of the unilateral jaw rest 414 on the right side of the patient's face. Similarly, if a user would like to tilt the patient's head to the left side during a procedure (for example, because the user is right-handed and needs to rotate the patient further to the left side to access the third molar tooth), the user can help support the patient's jaw on the left side with the device by attaching the jaw rest assembly 400 to the left side ball joint assembly 300, which positions the longer side of the unilateral jaw rest 414 on the left side of the patient's face.

A fourth embodiment of the jaw rest assembly 400, as illustrated in FIG. 17, can include a vertical support 416, a horizontal support 418, and a jaw support 420. These three components can be separate pieces that are combined, or they can be formed as one continuous piece. In some cases, the three components may be one, rigid interior that does not deform (for example, a metal or plastic). A compressible foam outer layer can be placed over the rigid interior to cover it and to allow flexibility for precise fitting to a patient's jaw. This outer layer can be disposable and can be available in various sizes to accommodate patients of various jaw sizes.

The vertical support 416 can be located behind the jaw and angled upward near the back of the jaw to hook around the back of the jaw (for example, it can run along a y-axis) and is useful if the user needs to pull the patient's jaw forward to open the airway. The horizontal support 418 can be a straight portion that is roughly parallel to the ground and the jaw line that rests along the bottom portion of the jaw (for example, it can run along a z-axis) and can operate to support the jaw when downward force is applied. The jaw support 420 can be a straight portion that is roughly parallel to the ground and roughly perpendicular to the jaw that rests along the bottom of the jaw (for example, it can run along an x-axis). Therefore, all three pieces together provide complete support to a patient's jaw. As described above, the jaw support device may have two sets of the split sphere assembly 200, ball joint assembly 300, and jaw rest assembly 400 so that both sides of a patient's jaw can be fully supported. Further, the fourth embodiment of the jaw rest assembly 400 having the vertical support 416, horizontal support 418, and jaw support 420 connected to the jaw rest connector 422 can be implemented on a first side of the patient, and a different embodiment of the jaw rest assembly 400 having, for example, the bilateral jaw rest 402 can be implemented on a second side of the patient.

In an example use case, when a user wishes to activate the jaw support device to hold a patient's jaw in place, the disclosed device can be activated and locked in a one- or two-lock process. In the unlocked phase, there is no locking mechanism activated and the user can position the device in the general position for the intended patient. When the user activates the locking mechanism (for example, by turning on the air or activating the magnetorheological fluid through use of a foot switch), the two-lock embodiment of the device can transition into a soft-lock phase by implementing a soft lock that holds the split sphere assembly 200 and ball joint assembly 300 roughly in place, but continues to allow a user to move the various components, albeit with some resistance. The user can, therefore, finesse the various components until they are in their precise locations, activate the full locking mechanism (for example, by increasing air pressure to 80 PSI), and the device will transition into a hard-lock phase by implementing a hard lock that keeps the split sphere ball 204 and ball joint ball 304 immobile, and therefore all components in place, until the full lock is released.

In a one-lock embodiment, when the user turns on the air or activates the magnetorheological fluid, the device transitions directly into a hard-lock phase that holds the split sphere assembly 200 and ball joint assembly 300 firmly in place. Therefore, the split sphere ball 204 and ball joint ball 304 are kept immobile until the full air pressure or magnetorheological fluid is released.

During positioning of one side of the device, the user can move the split sphere assembly 200, ball joint assembly 300, and jaw rest assembly 400, as a group, further outward from the head of the patient (or, conversely, closer to the patient's head) by moving the width adjustor 104 left or right along the first axis. As described above, the width lock 110 can lock the width adjustor 104 in place and prevent the split sphere assembly 200 from movement along the first axis during the procedure.

The user can then adjust the hollow tube arm 212, which is movable and rotatable due to its connection within the split sphere ball 204, to more precisely rotate the ball joint assembly 300 and jaw rest assembly 400 toward or away from the patient. For example, due to the nature of the split sphere ball 204 being a sphere and the hollow tube arm 212 being configured to exit from both the front and the back of the split sphere ball, the user can make adjustments of the assemblies 300, 400 by moving the hollow tube arm along three axes and by, as described above, rotating it around a central rotation axis for additional configuring. For example, as described above, the user can adjust the assemblies 300, 400 along the first axis corresponding to left/right movement; a second axis corresponding to up/down movement; and a third axis corresponding to front/back movement, wherein the hollow tube arm can slide forward and backward through the split sphere ball so that more or less of the arm is positioned in front of the split sphere ball.

In some embodiments, the first locking component (for example, the split sphere air valve 208) operates on a separate activation than the second locking component (for example, the ball joint air valve 216). Therefore, when the hollow tube arm 212 and split sphere ball 204 are in a desired position, the user can activate the split sphere air valve 208, which pushes the split sphere piston 206 against the split sphere ball 204 and forces the upper and lower halves 204*a*, 204*b* of the split sphere ball 204 to clamp down on the arm extension (for example, the hollow tube arm 212). This clamping motion creates the hard lock to hold the split sphere ball 204 and arm extension in place, while still allowing the user to move and configure portions of the ball joint assembly 300 and jaw rest assembly 400. However, in other embodiments, the split sphere air valve 208 and the ball joint air valve 216 operate on the same activation and, therefore, a single locking mechanism will lock both simultaneously. In that embodiment, the user will not want to activate the split sphere air valve 208 until ball joint ball 304 and the jaw rest assembly 400 are also appropriately positioned. As described above, a similar mechanism can take place by activating the magnetorheological fluid in the split sphere housing 202 and ball joint housing 302 via the split sphere electric connection 224 and ball joint electrical connection 222, respectively.

To finalize the remainder of the positioning (either before both locking mechanisms are simultaneously activated or between activation of the locking mechanisms if they are separately activated), the user can pull on the jaw rest assembly 400 and rotate it into a desired position due to its connection to the ball joint ball 304. When the jaw rest assembly 400 has been rotated into a desired position, the user can activate both locking mechanisms (if the activation is simultaneous) or just the first locking mechanism (if activation is separate), which forces the ball joint ball 304 into a secure position by either pushing the ball joint piston 306 against the ball joint ball 304 or increasing the viscosity of the magnetorheological fluid in the split sphere housing 202. This pressure is the final positioning step and creates the hard lock to hold the ball joint ball 304 in place. In some cases, if the jaw rest assembly 400 includes the vertical support 416, horizontal support 418, and/or jaw support 420 (see FIG. 17), activation of the locking mechanisms may not impact adjustability of the supports and may allow the user to move and configure the very precise angles of the three jaw support components.

Figure 14C:
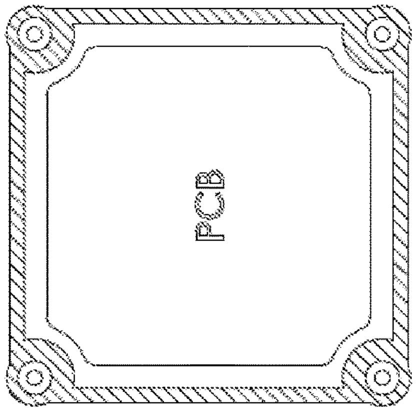
FIG. 14*c* is a cross-section view of the printed circuit board of FIG. 14*b* shown from the line C-C in FIG. 14*b*.

As described above, instead of an air locking mechanism, the jaw support device can lock using an alternative locking mechanism (for example, a magnetic or electric locking mechanism) that is controlled by a printed circuit board, as illustrated in FIG. 14*c*. For example, the split sphere housing 202 and ball joint housing 302 can each have an electrostatic magnet at their bases instead of, or in addition to, the corresponding split sphere piston 206 or ball joint piston 306. The split sphere ball 204 and ball joint ball 304 can be enclosed or partially enclosed within their respective housings 202, 302, and a magnetorheological fluid can act as a lubricant between the split sphere ball/ball joint ball and their respective housings on the inner bearing surface.

Figure 14B:
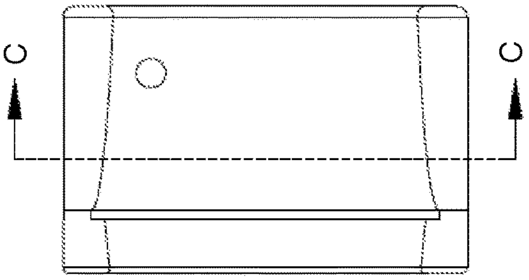
FIG. 14*b* illustrates an example printed circuit board.
Figure 14A:
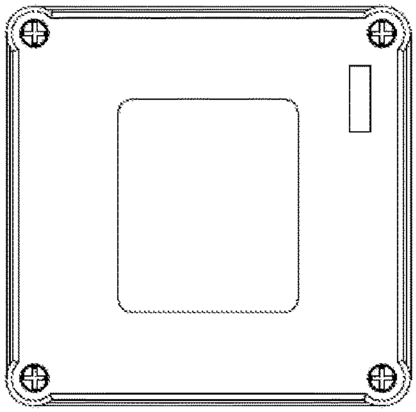
FIG. 14*a* illustrates an example control box.

The pneumatic control box, illustrated in FIG. 14*a*, and printed circuit board, illustrated in FIGS. 14*b*-14*c*, can be located on the back of the dental chair to keep it easily accessible. In some embodiments, the printed circuit board enclosure can be integrated with the jaw support device and, therefore, be closer to the headrest.

To control the magnetorheological fluid, the jaw support device may include an electromagnet and appropriate controls. Therefore, when the magnetorheological fluid is subjected to a magnetic field created by the electromagnet, the viscosity of the fluid will increase until it becomes a viscoelastic solid. Once the magnetorheological fluid because a viscoelastic solid, the split sphere ball 204 and ball joint ball 304 are effectively locked in position. After the dental or oral procedure is completed, removal of the electrical current from the electromagnet can deactivate the magnetic field, and the magnetorheological fluid can return to a flowable liquid state. This enables the split sphere ball 204 and ball joint ball 304 within their respective housings 202, 302 to once again move freely. In some embodiments, the jaw rest assembly 400 also contains magnetorheological fluid and is similarly adjustable. In other embodiments, activation of the magnetorheological fluid does not impact movement of the jaw rest assembly 400.

In one embodiment, the current can be activated and deactivated by a surgeon, dentist, or assistant using appropriate controls. For example, a user can control activation using a foot control pedal or a hand switch. This quick release is desirable for repositioning the patient during a procedure or surgery and it is also useful in the event of a power failure or emergency.

When the jaw support device is no longer needed (for example, when a procedure has been completed), the user can use the foot switch or other air activation/deactivation switch to turn the split sphere air valve 208 and ball joint air valve 216 off. Similarly, if a magnetic locking mechanism is used, a foot switch or other activation/deactivation switch can activate and deactivate the current to increase or decrease the viscosity of the magnetorheological fluid. This allows all components maximum movement, and the user can put the device into its stored position. More specifically, the user can pull the jaw rest assembly 400 away from the patient's jaw by rotating the ball joint ball 304 and, therefore, shifting the jaw rest assembly 400. The user can also put force on the hollow tube arm 212 and rotate it, along with the ball joint assembly 300 and jaw rest assembly 400, outward due to its connection to the rotatable split sphere ball 204.

The user can then push the width adjustor 104 inward along the first axis, if necessary, and can then rotate the split sphere housing 202 upward so the wide apertures of the split sphere housing are facing up and down. With the air or current off/deactivated, the hollow tube arm 212 can slide through the cylindrical aperture of the split sphere ball 204 until the ball joint assembly 300 is resting against the front wide aperture of the split sphere housing 202, as illustrated in FIG. 1. This positioning enables a patient to easily get in and out of the chair without bumping the jaw support device, and it keeps the jaw support device in a convenient, stored position when it is not needed.

Figure 18:
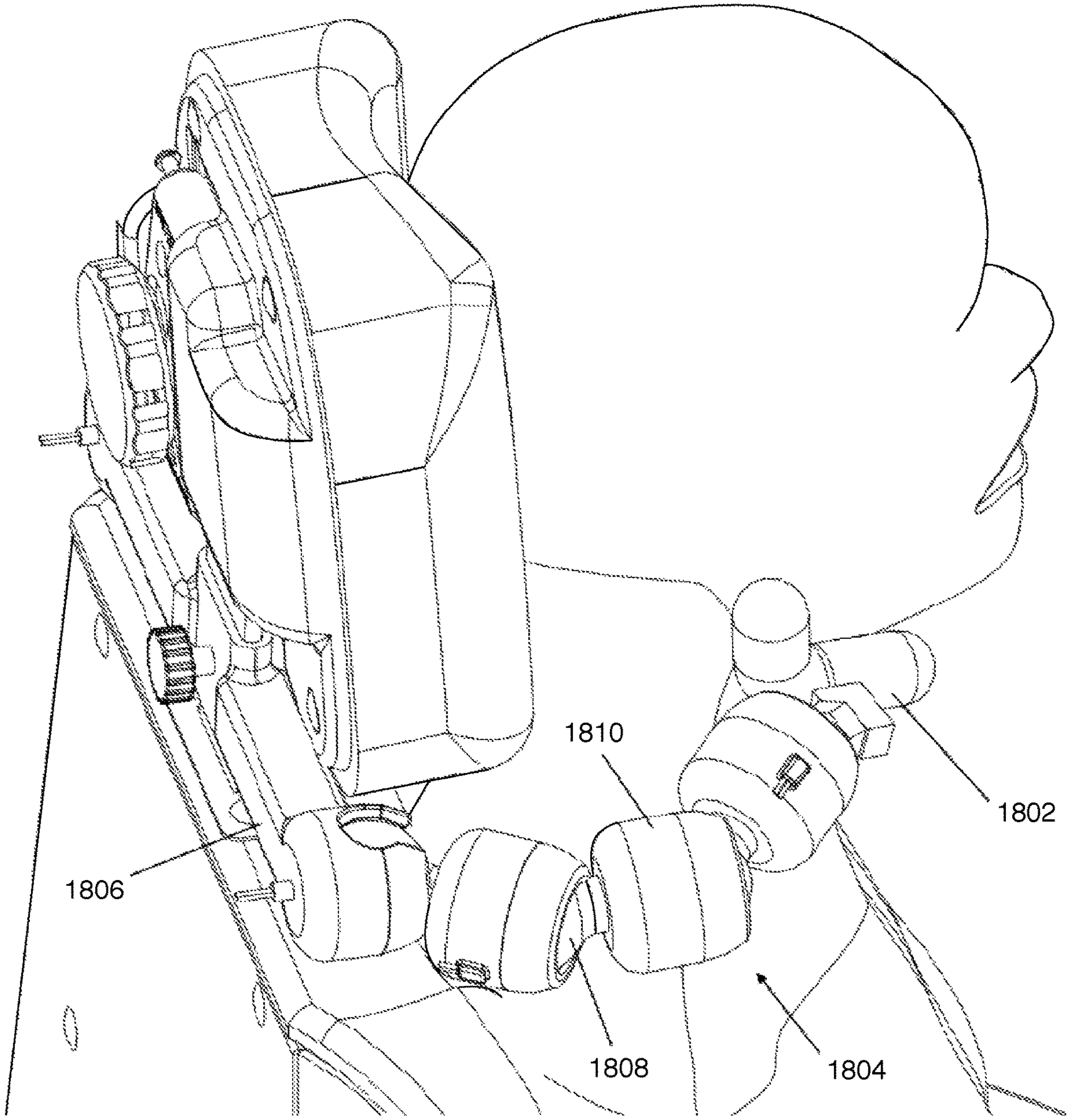
FIG. 18 is a back right perspective view of one embodiment of the disclosed jaw support device in use.

In some embodiments, the jaw support device, as illustrated in FIG. 18, can include one or more jaw rests 1802, adjustable arms 1804, and a headrest attachment 1806 that can be adjustable and that can be used with different sized headrest posts. The adjustable arms 1804 can attach, on one side, to the adjustable headrest attachment 1806 and, on the other side, to the jaw rest 1802.

In some embodiments, the jaw support device is comprised of two jaw rests 1802, as illustrated in FIGS. 20-21, which support the back of the jaw on each side. The shape of the jaw rest, in combination with each one's placement under and behind the sides of a patient's jaw, can move the patient's jaw into a forward position and open the patient's airway, which addresses any hypoxia issues that can occur with moderate/deep sedation or general anesthesia.

Figure 19:
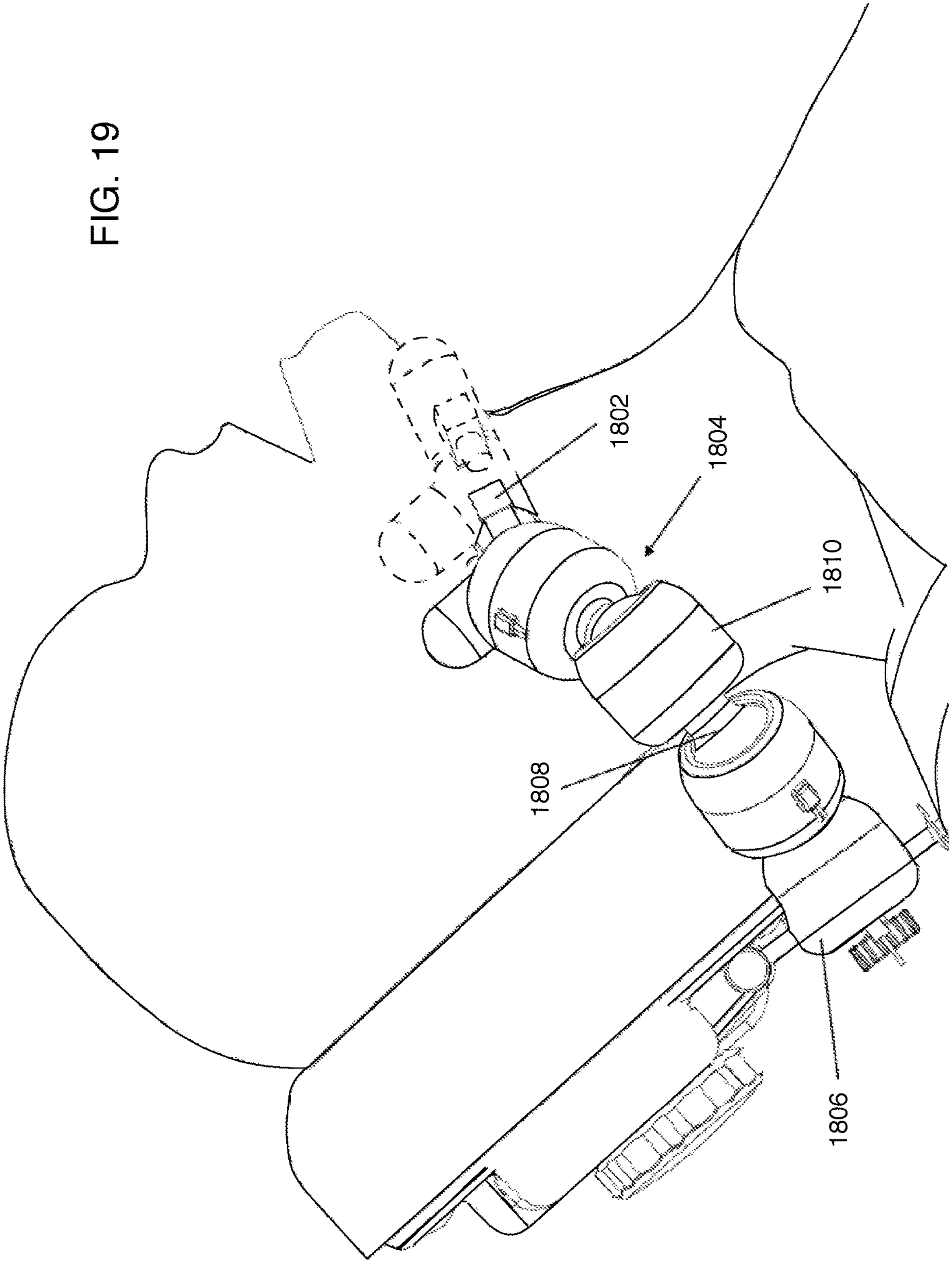
FIG. 19 is a right side view of one embodiment of the disclosed jaw support device in use and illustrates various positions of the jaw rest.

As illustrated in FIGS. 18-19, one or both of the two jaw rests 1802 can have an L-shaped structure. These jaw rests can be comprised of a rigid core and a pad, such as a compressible foam or other firm, yet viscoelastic material. Alternatively, the jaw rests can be comprised entirely of a firm, viscoelastic material. Further, the jaw rests may be adjustable or may be available in several sizes to accommodate different jaw sizes. The jaw rests 1802 can be attached to a ball joint and can, therefore, be adjustable, which allows for positioning the jaw rests 1802 to accommodate different jaw shapes and sizes.

The jaw rests 1802 can be shaped so that they can hook under and behind the jaw line, which allow the patient's jaw to be pushed forward during a dental procedure or surgery, as illustrated in FIG. 19, wherein the jaw rest 1802 is shown transitioning between its active and inactive positions. When the jaw rests 1802 are pushed forward, they ensure a patient's airway remains open during a procedure, which reduces the risk of emergencies due to hypoxia issues that can occur during moderate/deep sedation or general anesthesia.

In some embodiments, as illustrated in FIGS. 18-21, the adjustable arms 1804 can be comprised of a series of ball joints 1808 to allow for a full range of motion. For example, each adjustable arm 1804 can be comprised of four ball joints 1808 connected in line with each other, wherein the proximal end of the adjustable arm is comprised of a first ball joint that attaches to a headrest mount 1806, and the distal end of the adjustable arm is comprised of a last ball joint that attaches directly or indirectly to the jaw rest 1802. This embodiment accounts for the variability of patient jaw and face sizes. In some embodiments, each ball joint 1808 can have an electrostatic magnet at its base. The ball joints 1808 can be enclosed or partially enclosed within a ball socket 1810 and a magnetorheological fluid can act as a lubricant between the ball joints and ball sockets on the inner bearing surface.

As described above, to control the magnetorheological fluid, the jaw support device may include an electromagnet and appropriate controls. Therefore, when the magnetorheological fluid is subjected to a magnetic field created by the electromagnet, the viscosity of the fluid will increase until it becomes a viscoelastic solid. Once the magnetorheological fluid because a viscoelastic solid, the ball joints 1808 are effectively locked in position. After the dental or oral procedure is completed, removal of the electrical current from the electromagnet can deactivate the magnetic field, and the magnetorheological fluid can return to a flowable liquid state. This enables the ball joints 1808 within the ball sockets 1810 to once again move freely. In some embodiments, the jaw rest 1802 also contains magnetorheological fluid and is similarly adjustable. In other embodiments, activation of the magnetorheological fluid does not impact movement of the jaw rest. As described above, the current can be activated and deactivated by a surgeon, dentist, or assistant using appropriate controls. For example, a user can control activation using a foot control pedal or a hand switch.

As mentioned above, the adjustable arms 1804 can attach to the dental chair via an adjustable headrest mount 1806. The adjustable headrest mount 1806 can attach to the neck portion of the dental chair headrest or it can attach directly to the back of the headrest. In some embodiments the adjustable headrest mount 1806 can be positioned higher or lower on the dental chair using a friction lock, which can be controlled by a knob. Therefore, when the knob is turned in one direction, it loosens the lock and enables the headrest mount 1806 to move along the neck portion or headrest. When the knob is turned in the opposite direction, it tightens the lock and can hold the headrest mount 1806 in place. In some embodiments, the headrest mount 1806 can also include the first ball joint and ball socket for each of the adjustable arms 1804.

Therefore, in one embodiment, as illustrated in FIGS. 18-21, the jaw support device can include an adjustable headrest mount having two adjustable arms 1804 attached to it on its ends, wherein each adjustable arm 1804 is comprised of a first, proximal ball joint and ball socket, a second ball joint and ball socket attached to the first ball joint and ball socket and attached to a third ball joint and ball socket, and a fourth, distal ball joint and ball socket attached to the third ball joint and ball socket as well as the jaw rest 1802.

The various embodiments described above are provided by way of illustration only and should not be construed to limit the claims attached hereto. Those skilled in the art will readily recognize various modifications and changes that may be made without following the example embodiments and applications illustrated and described herein and without departing from the true spirit and scope of the following claims.

What is claimed is:

1. A jaw support device, comprising:

a headrest mount assembly structured and configured to attach to a dental chair headrest;

a split sphere assembly comprising a first locking mechanism, a split sphere housing that contains a split sphere ball, and an arm extension, wherein the split sphere housing directly attaches to the headrest mount assembly;

a ball joint assembly comprising a second locking mechanism, wherein the ball joint assembly connects to the split sphere assembly; and a jaw rest assembly structured and configured to attach to the ball joint assembly, wherein the first locking mechanism and the second locking mechanism are simultaneously activated and deactivated using a single activation system, the split sphere housing is rotatable between a horizontal and a vertical configuration at its attachment point to the headrest mount assembly, and in the vertical configuration, the arm extension is vertically upright, enabling the arm extension to slide down through the split sphere housing for storage purposes.

2. The jaw support device of claim 1, wherein:

the split sphere ball is comprised of two separate halves;

the split sphere housing that completely contains the split sphere ball;

the first locking mechanism is structured and configured to lock the arm extension in place;

the ball joint assembly further comprises a ball joint ball within a ball joint housing, wherein the ball joint assembly connects to the split sphere assembly via the arm extension; and the second locking mechanism is structured and configured to lock the jaw rest assembly in place.

3. The jaw support device of claim 2, wherein:

the two separate halves of the split sphere ball are an upper half and a lower half;

the upper half and the lower half are each dome-shaped;

the split sphere ball has a cylindrical aperture through its center; and the arm extension fits within the cylindrical aperture.

4. The jaw support device of claim 1, wherein:

the split sphere housing has a front aperture and a back aperture;

the split sphere ball has a cylindrical aperture through its center;

the cylindrical aperture aligns with the front aperture and the back aperture; and in the vertical configuration of the split sphere housing, the front aperture faces upward and the back aperture faces downward relative to the dental chair headrest.

5. The jaw support device of claim 3, wherein:

a split sphere piston is located beneath the split sphere ball within the split sphere housing;

activation of the first locking mechanism causes the upper half and the lower half of the split sphere ball to clamp down on the arm extension and lock it in place.

6. The jaw support device of claim 1, wherein:

the first locking mechanism is structured and configured to lock the arm extension in place;

the ball joint assembly further comprises a ball joint ball within a ball joint housing;

the ball joint ball includes a ball joint rod;

the ball joint housing is cylindrical in shape with a solid outer face, an inner face having an aperture through which the ball joint rod of the ball joint ball protrudes, a curved outer circumference, and a tube arm connector that protrudes from a portion of the curved outer circumference;

the arm extension is a hollow tube arm that connects to the tube arm connector of the ball joint housing;

the ball joint rod connects to a jaw rest connector of the jaw rest assembly; and activation of the second locking mechanism locks the ball joint ball in place, which in turn directly locks the jaw rest assembly in place.

7. The jaw support device of claim 6, wherein the jaw rest assembly is comprised of a jaw rest having a rigid main body, the jaw rest connector, and a padded surface that wraps around the rigid main body.

8. The jaw support device of claim 6, wherein a ball joint piston is located beneath the ball joint ball within the ball joint housing.

9. The jaw support device of claim 2, wherein the jaw rest assembly includes a jaw rest having:

a jaw rest connector having a first end connecting the jaw rest to the ball joint assembly;

a main body connecting to a second end of the jaw rest connector; and a padded surface covering at least one side of the main body.

10. The jaw support device of claim 2, wherein the first locking mechanism and the second locking mechanism are pneumatic air locking mechanisms.

11. The jaw support device of claim 2, wherein the first locking mechanism and the second locking mechanism are magnetic locking mechanisms.

12. The jaw support device of claim 2, wherein the first locking mechanism and the second locking mechanism are electric locking mechanisms.

13. The jaw support device of claim 2, further comprising:

a second split sphere assembly comprising:

a second split sphere ball comprised of two separate halves, a second split sphere housing that completely contains the second split sphere ball, a second arm extension, and a third locking mechanism structured and configured to lock the second arm extension in place, wherein the second split sphere housing directly attaches to the headrest mount assembly;

a second ball joint assembly comprising:

a second ball joint ball within a second ball joint housing, and a fourth locking mechanism, wherein the second ball joint assembly connects to the second arm extension; and a second jaw rest assembly structured and configured to attach to the second ball joint assembly, wherein the fourth locking mechanism is structured and configured to lock the second jaw rest assembly in place, wherein the third locking mechanism and the fourth locking mechanism are simultaneously activated and deactivated using the single activation system.

14. The jaw support device of claim 13, wherein:

the headrest mount assembly has a first end and a second end;

the split sphere housing attaches to the first end of the headrest mount assembly;

the second split sphere housing attaches to the second end of the headrest mount assembly; and the first, second, third, and fourth locking mechanisms are simultaneously activated and deactivated using the single activation system.

15. A jaw support device, comprising:

a headrest mount assembly structured and configured to attach to a dental chair headrest;

a split sphere assembly comprising:

a split sphere ball completely contained within a split sphere housing, the split sphere ball having an upper half and a separate lower half, an arm extension located between the upper half and the lower half of the split sphere ball, and a first locking mechanism structured and configured to lock the arm extension within the upper half and the lower half of the split sphere ball, wherein the split sphere housing directly attaches to the headrest mount assembly;

a ball joint assembly comprising:

a ball joint ball within a ball joint housing, and a second locking mechanism, wherein the ball joint assembly connects to the split sphere assembly via the arm extension; and a jaw rest assembly structured and configured to attach to the ball joint assembly, wherein the second locking mechanism is structured and configured to lock the jaw rest assembly in place, wherein the first locking mechanism and the second locking mechanism are simultaneously activated and deactivated using a single activation system, wherein the split sphere housing is rotatable between a horizontal and a vertical configuration at its attachment point to the headrest mount assembly, and wherein in the vertical configuration, the arm extension is vertically upright, enabling the arm extension to slide down through the split sphere housing for storage purposes.

16. The jaw support device of claim 12, wherein the first locking mechanism and the second locking mechanism are activated and deactivated by a foot control pedal.

17. The jaw support device of claim 12, wherein the first locking mechanism and the second locking mechanism are activated and deactivated by a hand switch.

18. The jaw support device of claim 1, wherein:

the split sphere housing that completely contains the split sphere ball, the arm extension connects to the split sphere ball, the split sphere ball is comprised of two separate halves, an upper half and a lower half;

the split sphere housing is cylindrical in shape, has flat, solid top and bottom faces that are free of apertures, and has a curved circumference having openings;

the openings in the split sphere housing are a front aperture on a front facing portion of the curved circumference and a back aperture on a back facing portion of the curved circumference;

the split sphere ball has a cylindrical aperture through its center;

the cylindrical aperture of the split sphere ball aligns with the front aperture and the back aperture of the split sphere housing;

the arm extension fits within the cylindrical aperture of the split sphere ball and extends out of the front aperture and the back aperture of the split sphere housing;

activation of the first locking mechanism causes the upper half and the lower half of the split sphere ball to clamp down on the arm extension and lock it in place.

19. The jaw support device of claim 18, wherein:

a split sphere piston is located beneath the split sphere ball within the split sphere housing;

a split sphere housing air cavity is located beneath the split sphere piston within the split sphere housing;

an outer circumference of the split sphere piston has a channel that houses an o-ring, activation of the first locking mechanism causes the split sphere piston to push up against a bottom of the lower half of the split sphere ball, which moves toward the upper half of the split sphere ball and causes the arm extension to be locked in place between the upper half and the lower half.

20. The jaw support device of claim 19, wherein:

the ball joint assembly further comprises a ball joint ball within a ball joint housing, the ball joint ball includes a ball joint rod;

the ball joint housing is cylindrical in shape with a flat, solid outer face, a flat inner face having an aperture through which the ball joint rod of the ball joint ball protrudes, a curved outer circumference, and a tube arm connector that protrudes from a portion of the curved outer circumference;

the arm extension is a hollow tube arm that connects to the tube arm connector of the ball joint housing;

the jaw rest assembly is comprised of a jaw rest having a rigid main body, a jaw rest connector, and a padded surface that covers at least one side of the rigid main body;

the ball joint rod connects to the jaw rest connector;

activation of the second locking mechanism locks the ball joint ball in place, which in turn directly locks the jaw rest assembly in place.

* * * * *